(12) United States Patent
Wang et al.

(10) Patent No.: US 10,385,059 B2
(45) Date of Patent: Aug. 20, 2019

(54) ORGANIC ELECTROLUMINESCENT MATERIAL AND ORGANIC OPTOELECTRONIC DEVICE

(71) Applicants: Shanghai Tianma AM-OLED Co., Ltd., Shanghai (CN); Tianma Micro-Electronics Co., Ltd., Shenzhen (CN)

(72) Inventors: Xiangcheng Wang, Shanghai (CN); Ying Liu, Shanghai (CN); Hongyang Ren, Shanghai (CN); Wei He, Shanghai (CN); Chen Liu, Shanghai (CN)

(73) Assignees: Shanghai Tianma AM-OLED Co., Ltd., Shanghai (CN); Tianma Micro-Electronics Co., Ltd., Shenzhen (CN)

( * ) Notice: Subject to any disclaimer, the term of this patent is extended or adjusted under 35 U.S.C. 154(b) by 258 days.

(21) Appl. No.: 15/600,987

(22) Filed: May 22, 2017

(65) Prior Publication Data

US 2017/0256716 A1    Sep. 7, 2017

(30) Foreign Application Priority Data

Dec. 30, 2016    (CN) .......................... 2016 1 1264917

(51) Int. Cl.
*H01L 51/50*    (2006.01)
*C07D 487/14*    (2006.01)
(Continued)

(52) U.S. Cl.
CPC ............ *C07D 487/14* (2013.01); *C09K 11/06* (2013.01); *H01L 51/0071* (2013.01);
(Continued)

(58) Field of Classification Search
None
See application file for complete search history.

(56) References Cited

FOREIGN PATENT DOCUMENTS

CN    103483332 A    1/2014
CN    105254555 A    1/2016
(Continued)

*Primary Examiner* — Gregory D Clark
(74) *Attorney, Agent, or Firm* — Anova Law Group, PLLC

(57) ABSTRACT

A compound and an organic optoelectronic device are provided. The compound has the following chemical formula (I):

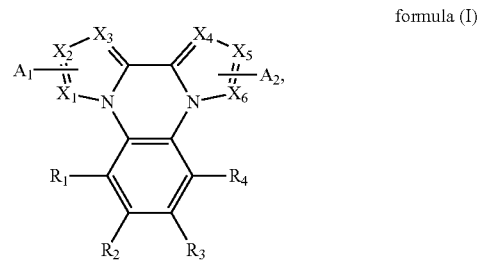

formula (I)

wherein: in the chemical formula (I), $R_1$ to $R_{10}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, $X_1$ to $X_6$ are independently selected from C and N, when N is selected, N does not include a substituent, and when C is selected, C includes a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, at least one of $X_1$ to $X_3$ and at least one of $X_4$ to $X_6$ are selected as C and, meanwhile, connected to $A_1$ and $A_2$, respectively, and $A_1$ and $A_2$ are chemical groups independently represented by the following chemical formula (II):

(Continued)

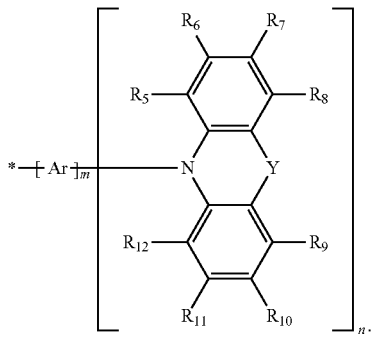

formula (II)

(51) Int. Cl.
*C09K 11/06* (2006.01)
*H01L 51/00* (2006.01)

(52) U.S. Cl.
CPC ...... *H01L 51/0072* (2013.01); *H01L 51/5012* (2013.01); *H01L 51/5016* (2013.01)

(56) References Cited

FOREIGN PATENT DOCUMENTS

CN 105418617 A * 3/2016 ............. H01L 51/50
WO 2016116504 A1 7/2016

* cited by examiner

19 Claims, 4 Drawing Sheets

ORGANIC ELECTROLUMINESCENT MATERIAL AND ORGANIC OPTOELECTRONIC DEVICE

CROSS-REFERENCES TO RELATED APPLICATIONS

This application claims priority of Chinese Patent Application No. 201611264917.8, filed on Dec. 30, 2016, the entire contents of which are hereby incorporated by reference.

FIELD OF THE DISCLOSURE

The present disclosure generally relates to the field of organic electroluminescent material, and, more particularly, relates to an organic electroluminescent material and an organic optoelectronic device thereof.

BACKGROUND

Recently, organic light-emitting diodes (OLEDs) are emerging as a new generation of display products, because of various advantages such as self-luminous, high efficiency, wide color gamut, and wide viewing angle. Organic electroluminescent materials play a critical role for the continuous development of OLEDs.

The organic electroluminescent materials can be excited to generate singlet excited state ($S_1$) excitons and triplet excited state ($T_1$) excitons. According to the spin statistics, the ratio of the $S_1$ excitons to the $T_1$ excitons is 1:3. According to different light-emitting mechanisms, the existing organic electroluminescent materials are often categorized into fluorescent materials, phosphorescent materials, triplet-triplet annihilation (TTA) materials, and heat activated delayed fluorescence (TADF) materials.

TADF materials have the advantages of high quantum yield and low production cost, and comparable luminous efficiency as the phosphorescent material. TADF materials are expected to be new organic electroluminescent materials with great applications. However, the choices of the existing TADF materials are rather limited, and the performance of the TADF materials has not been improved yet. Diverse and high performance TADF materials are highly desired.

The disclosed organic electroluminescent material and organic optoelectronic device thereof are directed to solve one or more problems set forth above and other problems.

BRIEF SUMMARY OF THE DISCLOSURE

One aspect of the present disclosure provides a compound of the following chemical formula (I):

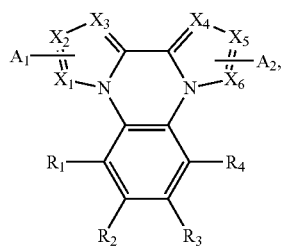

formula (I)

wherein: in the chemical formula (I), $R_1$ to $R_{10}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, $X_1$ to $X_6$ are independently selected from C and N, when N is selected, N does not include a substituent, and when C is selected, C includes a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, at least one of $X_1$ to $X_3$ and at least one of $X_4$ to $X_6$ are selected as C and, meanwhile, connected to $A_1$ and $A_2$, respectively, and $A_1$ and $A_2$ are chemical groups independently represented by the following chemical formula (II):

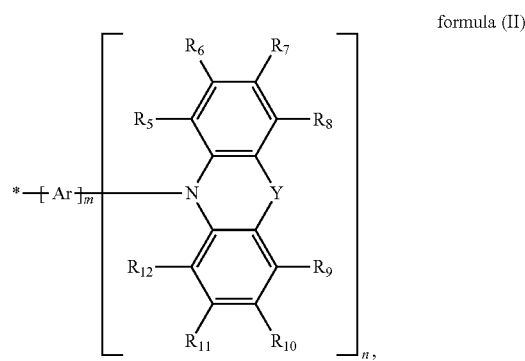

formula (II)

wherein: in the chemical formula (II), $R_5$ to $R_{12}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, Y is selected from O, S, substituted or unsubstituted imino, substituted or unsubstituted methylene, substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl, Ar is selected from $C_6$ to $C_{30}$ aryl and $C_2$ to $C_{30}$ heteroaryl, m represents 0 or 1, and n represents 0 or 1, and n in $A_1$ and n in $A_2$ are not zero at the same time.

Another aspect of the present disclosure provides an organic optoelectronic device. The organic optoelectronic device comprises an anode; a cathode; and one or more organic thin film layers disposed between the anode and the cathode. At least one of the one or more organic thin film layers includes one or more disclosed compounds.

Other aspects of the present disclosure can be understood by those skilled in the art in light of the description, the claims, and the drawings of the present disclosure.

BRIEF DESCRIPTION OF THE DRAWINGS

The following drawings are merely examples for illustrative purposes according to various disclosed embodiments and are not intended to limit the scope of the present disclosure.

In FIGS. 1-5 and 7, the various reference numerals and corresponding names are as follows: 100—substrate; 110—anode; 120—cathode; 130—light-emitting layer; 140—hole transport layer (HTL); 150—electron transport layer (ETL); 160—hole injection layer (HIL); 170—electron injection layer (EIL); 180—electron blocking layer (EBL); and 190—hole blocking layer (HBL).

DETAILED DESCRIPTION

Figure 1:
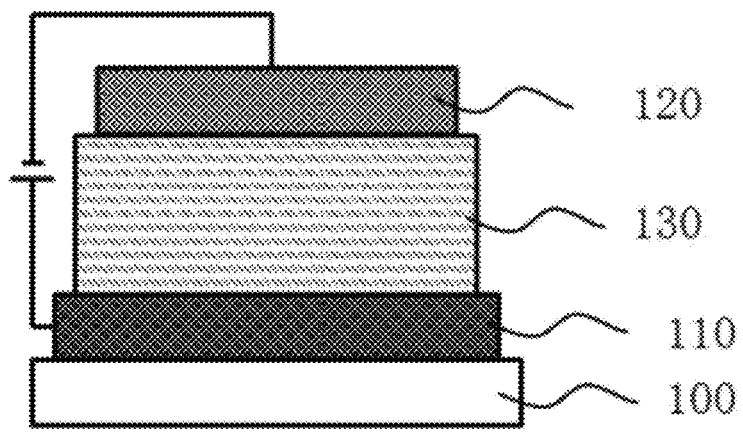
FIG. 1 illustrates a schematic diagram of an exemplary organic light-emitting diode (OLED) consistent with disclosed embodiments.

Reference will now be made in detail to exemplary embodiments of the disclosure, which are illustrated in the accompanying drawings. Hereinafter, embodiments consistent with the disclosure will be described with reference to drawings. In the drawings, the shape and size may be exaggerated, distorted, or simplified for clarity. Wherever possible, the same reference numbers will be used throughout the drawings to refer to the same or like parts, and a detailed description thereof may be omitted.

Further, in the present disclosure, the disclosed embodiments and the features of the disclosed embodiments may be combined under conditions without conflicts. It is apparent that the described embodiments are some but not all of the embodiments of the present disclosure. Based on the disclosed embodiments, persons of ordinary skill in the art may derive other embodiments consistent with the present disclosure, all of which are within the scope of the present disclosure.

As discussed in the background, according to different light-emitting mechanisms, the existing organic electroluminescent materials are often categorized into fluorescent materials, phosphorescent materials, triplet-triplet annihilation (TTA) materials, and heat activated delayed fluorescence (TADF) materials. In fluorescent materials, S1 excitons transit to the ground state $S_0$ by radiation, thereby emitting light. The material cost is substantially low, however, due to the limited number of $S_1$ excitons (i.e., accounting for 25% of the excitons generated by the organic electroluminescent material), the quantum efficiency is substantially low.

Phosphorescent materials not only utilize $S_1$ excitons accounting for 25% of the excitons generated by the organic electroluminescent material, but also utilize $T_1$ excitons accounting for 75% of the excitons generated by the organic electroluminescent material. Thus, the theoretical quantum efficiency of phosphorescent materials is up to 100%, and when used as organic electroluminescent materials for the OLEDs, the phosphorescent materials has significantly improved the luminous efficiency as compared to the fluorescent materials. However, the phosphorescence materials are limited to Ir, Pt, Os, Re, Ru and other heavy metal complexes. The production cost is higher, and the structure is substantially simple.

TTA materials utilize two $T_1$ excitons interactions to produce one $S_1$ exciton that transitions back to the ground state $S_0$ by radiation. Although $T_1$ excitons are utilized, the production cost is not high, and the theoretical maximum quantum yield of TTA materials is only about 62.5%. The practical applications of TTA materials are still rather limited.

TADF materials utilize both $S_1$ excitons accounting for 25% of the excitons generated by the organic electroluminescent material, and $T_1$ excitons accounting for 75% of the excitons generated by the organic electroluminescent material. Thus, the theoretical quantum efficiency of TTA materials is up to 100%. TADF materials are mainly aromatic organic materials without rare metal elements, and the production cost is substantially low.

According to the above discussion of various existing organic electroluminescent materials, TADF materials have high quantum yield, low production cost, and comparable luminous efficiency as the phosphorescent material. TADF materials are expected to be organic electroluminescent materials with great application prospect. However, the choices of the existing TADF materials are rather limited, and the performance the TADF materials has to be improved. Diverse and high performance TADF materials are highly desired.

The present disclosure provides an organic electroluminescent material to be used in an organic optoelectronic device, and an organic optoelectronic device thereof.

Unless otherwise defined, all technical and scientific terms used herein have the same meaning as commonly understood by one of ordinary skill in the art to which this disclosure belongs. In case of conflict, the present specification, including definitions, will control. In addition, the materials, methods, and examples are for illustrative only and not intended to limit the scope of the present disclosure.

When no other definition is provided, the term "substituted" used herein means that the hydrogen of the compound is substituted with at least one of the following groups: halogen (F, Cl, Br or I), hydroxy, alkoxy, nitro, cyano, amino, azido, amidino, nitrile, carbonyl, carbamoyl, thiol, ester, carboxyl or salt thereof, sulfonic acid group or salt thereof, phosphoric acid group or salt thereof, $C_1$ to $C_{30}$ alkyl group, $C_2$ to $C_{20}$ alkenyl group, $C_2$ to $C_{20}$ alkynyl group, $C_6$ to $C_{30}$ aryl group, $C_7$ to $C_{20}$ aralkyl group, $C_1$ to $C_8$ alkoxy group, $C_3$ to $C_{20}$ heteroaryl group, and $C_3$ to $C_{30}$ cycloalkyl.

Alkyl group refers to a hydrocarbyl group that is fully saturated (without double or triple bond), which may be linear or branched, or cycloalkyl, and may also be a straight or branched chain containing a cycloalkyl substituent chain. The alkyl group may contain 1 to 30 carbon atoms, 1 to 20 carbon atoms, 1 to 10 carbon atoms or 1 to 6 carbon atoms. The numerical range of "1 to 30" refers to all integers in the range, including 1, 2, 3, 4, 5, 6, 7, 8, 9, 10, 11, 12, 13, 14, 15, 16, 17, 20, 21, 22, 23, 24, 25, 26, 27, 28, 29 or 30. The alkyl group may include, but not limited to, methyl, ethyl, propyl, isopropyl, n-butyl, isobutyl, sec-butyl, tert-butyl, pentyl and hexyl. The alkyl group may be substituted or unsubstituted.

Heteroatom-substituted alkyl group includes an alkyl group substituted at any position by a heteroatom. For example, the heteroatom-substituted alkyl group may be attached to the compound nucleus by a heteroatom, i.e., in a "—Z-alkyl" form, where Z may represent a heteroatom such as 0 (i.e., oxygen atom), S (i.e., sulfur atom). The heteroatom-substituted alkyl group may also be an alkoxy group. The heteroatom-substituted alkyl group may include 1 to 30 carbon atoms, 1 to 20 carbon atoms, 1 to 10 carbon atoms or 1 to 6 carbon atoms. The numerical range of "1 to 30" refers to all integers in the range, including 1, 2, 3, 4, 5, 6, 7, 8, 9, 10, 11, 12, 13, 14, 15, 16, 17, 20, 21, 22, 23, 24, 25, 26, 27, 28, 29 or 30. The alkoxy group may include, but not limited to, methoxy, ethoxy, propoxy, isopropoxy, and butoxy. The heteroatom-substituted alkyl group may be substituted or unsubstituted.

Aromatic or Aryl group refers to carbocyclic (all carbon) having a completely delocalized π-electron system over all rings, including monocyclic aromatic or polycyclic aromatic groups. The polycyclic aromatic group may include two or more aromatic rings, such as a benzene ring, which are linked to each other by a single bond or by mutual chemical bonds. The number of carbon atoms in the aryl group may vary. For example, the aryl group may contain 6 to 30 carbon atoms. For example, a numerical range of 6 to 30 refers to all integers in the range, including 6, 7, 8, 9, 10, 11, 12, 13, 14, 15, 16, 17, 18, 19, 20, 21, 22, 23, 24, 25, 26, 27, 28, 29 or 30. The aryl group may include, but be not limited to, benzene, biphenyl, naphthalene, anthracene, phenanthrene or pyrene. The aryl group may be substituted or unsubstituted.

Heteroaryl group refers to a monocyclic or polycyclic aromatic ring system comprising one or more heteroatoms in which the heteroatoms are elements other than carbon, including but not limited to nitrogen, oxygen and sulfur. The number of carbon atoms in the heteroaryl ring may vary. For example, the heteroaryl group may include 1 to 20 carbon atoms in the ring, and a numerical range of 1-20 refers to all integers in the range, including 1, 2, 3, 4, 7, 8, 9, 10, 11, 12, 13, 14, 15, 16, 17, 18, 19 or 20. For example, the heteroaryl group may include 1 to 30 ring skeleton atoms in its ring, for example, a numerical range of 1-30 refers to all integers in the range, including 1, 2, 3, 11, 12, 13, 14, 15, 16, 17, 18, 19, 20, 21, 22, 23, 24, 25, 26, 27, 28, 29 or 30.

In addition, the heteroaryl group may include a fused ring system in which two rings, such as at least one aryl ring and at least one heteroaryl ring or at least two heteroaryl rings, share at least one chemical bond. For example, the heteroaryl ring may include, but not limited to, furan, furazan, thiophene, benzothiophene, phthalazine, pyrrole, oxazole, benzoxazole, 1,2,3-oxadiazole, oxadiazole, thiazole, 1,2,3-thiadiazole, 1,2,4-thiadiazole, benzothiazole, imidazole, benzimidazole, indole, indazole, pyrazole, benzopyrazole, Isoxazole, benzisoxazole, isothiazole, triazole, benzotriazole, thiadiazole, tetrazole, pyridine, pyridazine, pyrimidine, pyrazine, purine, pteridine, quinoline, isoquinoline, auinazoline, quinoxaline, cinnoline and triazine. The heteroaryl may be substituted or unsubstituted.

The present disclosure provides an organic electroluminescent material comprising a compound of the following chemical formula (I):

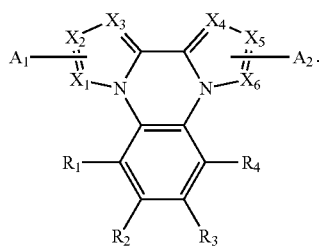

chemical formula (I)

In the chemical formula (I), $R_1$ to $R_{10}$ may be independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. $X_1$ to $X_6$ may be independently selected from C and N, when N is selected, N may not include a substituent, while when C is selected, C may include a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl.

Further, at least one of $X_1$ to $X_3$ may be selected as C and, meanwhile, connected to $A_1$. At least one of $X_4$ to $X_6$ may be selected as C and, meanwhile, connected to $A_2$. $A_1$ and $A_2$ may be chemical groups independently represented by the following chemical formula (II):

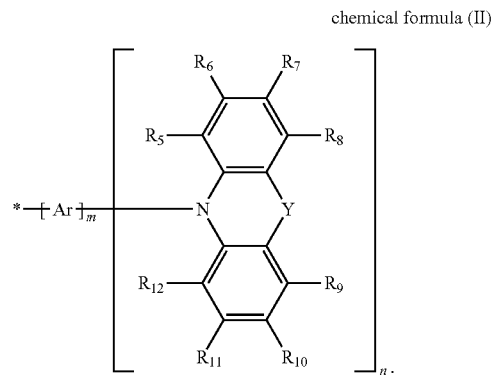

chemical formula (II)

In the chemical formula (II), $R_5$ to $R_{12}$ may be independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl. Y may be selected from O, S, substituted or unsubstituted imino, substituted or unsubstituted methylene, substituted or unsubstituted silylene, in which a substituent may be selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl.

Ar may be selected from $C_6$ to $C_{30}$ aryl and $C_2$ to $C_{30}$ heteroaryl. m represents 0 or 1, and n represents 0 or 1. n in $A_1$ and n in $A_2$ may not be zero at the same time.

In certain embodiments, the disclosed compounds may be represented by the following chemical formula (III):

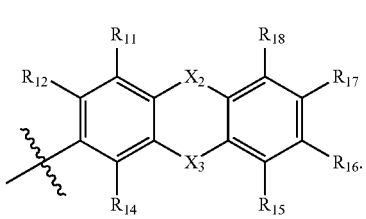

chemical formula (III)

In one embodiment, Y may be selected from O, S, —C(CH$_3$)$_2$—, —C(Ph)$_2$-, and —Si (CH$_3$)$_2$—.

In one embodiment, the $C_6$ to $C_{30}$ aryl group may be selected from phenyl and naphthyl.

In one embodiment, m in $A_1$ and m in $A_2$ may be 1 at the same time.

In one embodiment, n in $A_1$ and n in $A_2$ may be 1 at the same time.

Certain examples of the disclosed compounds are shown below as Compounds 1-35, which are for illustrative purposes and are not intended to limit the scope of the present discourse.

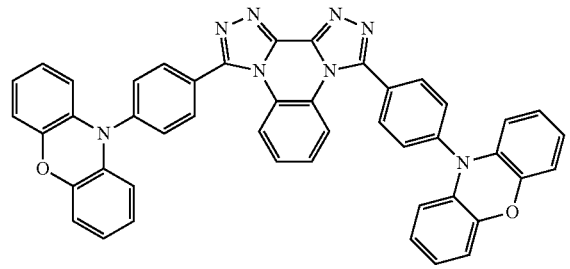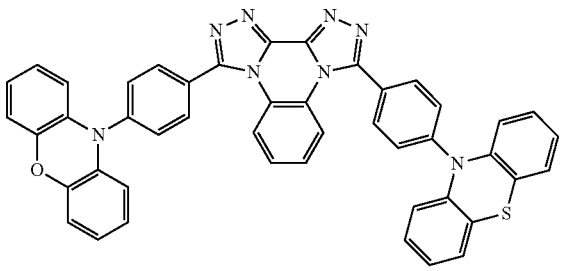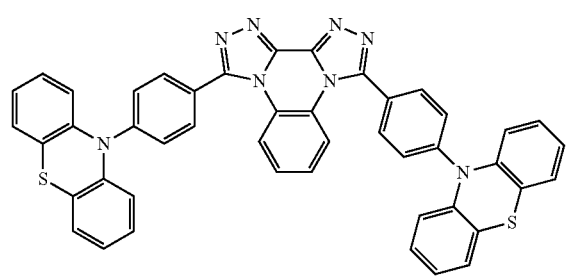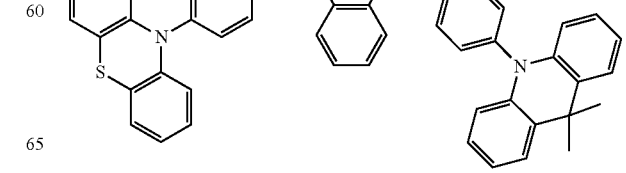

11
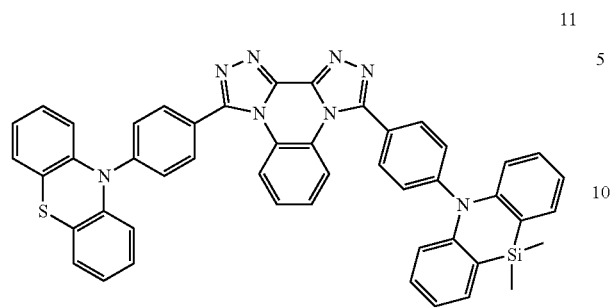
12
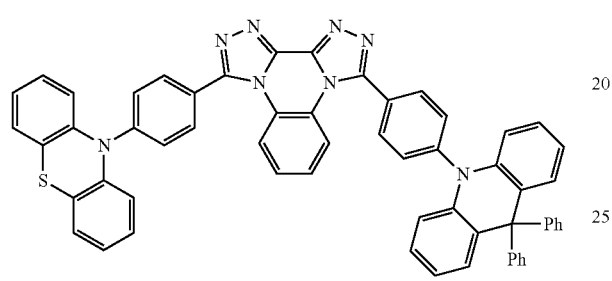
13
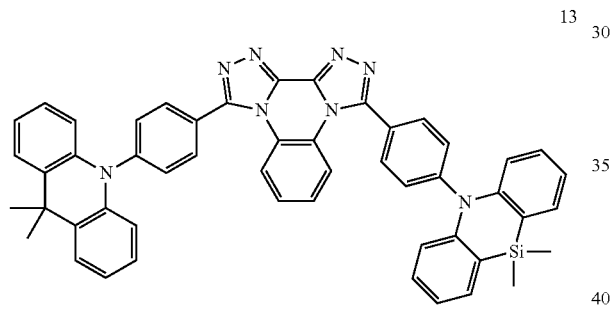
14
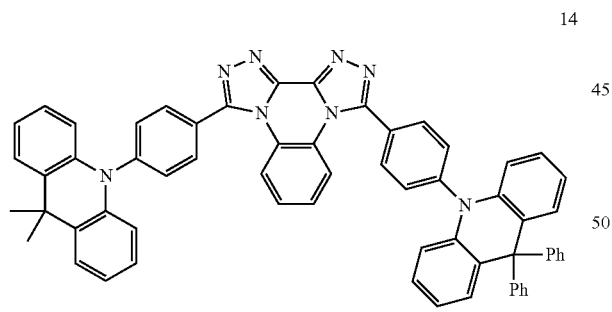
15
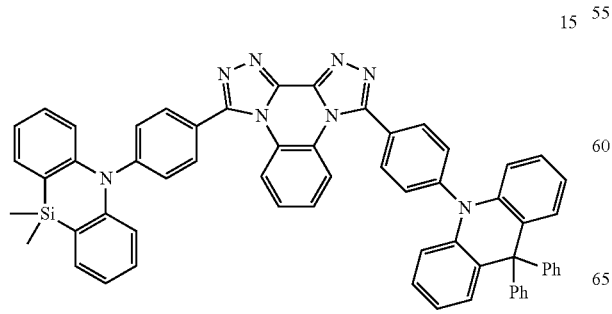
16
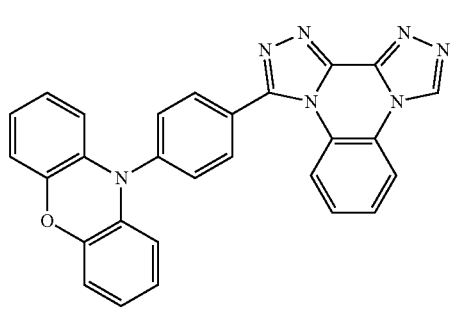
17
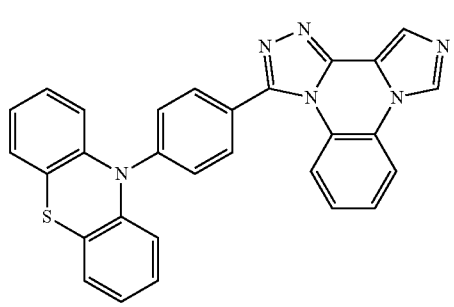
18
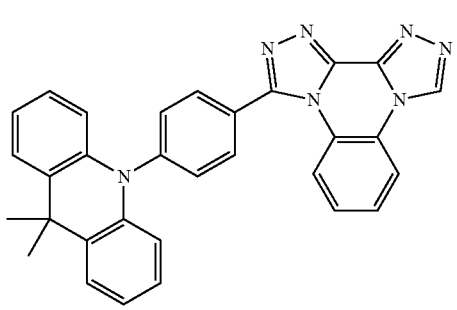
19
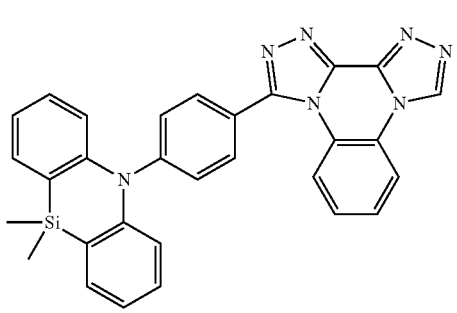
20
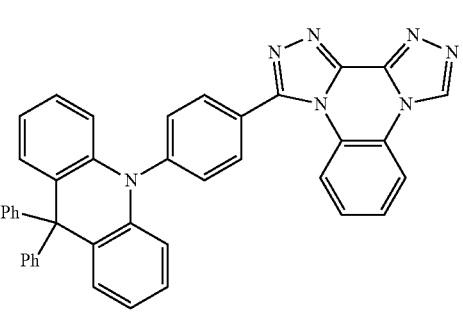

21
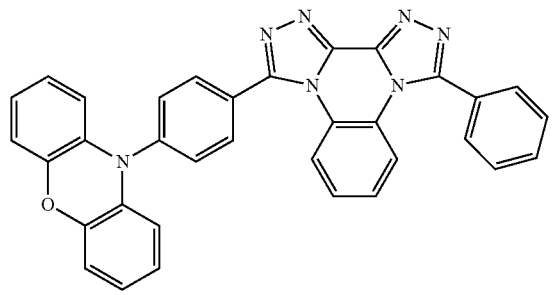
22
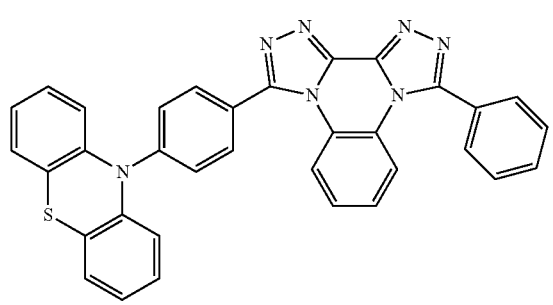
23
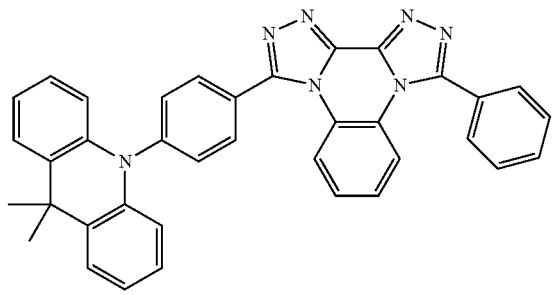
24
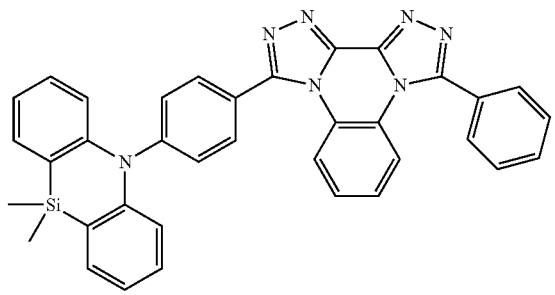
25
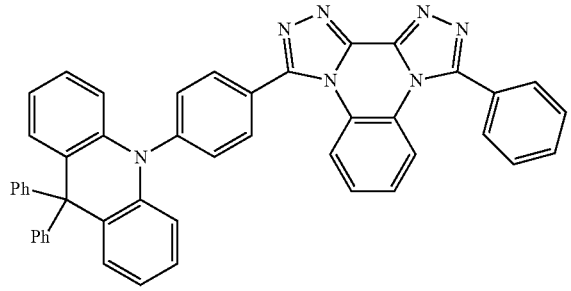
26
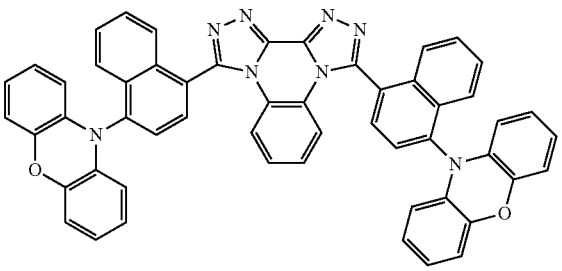
27
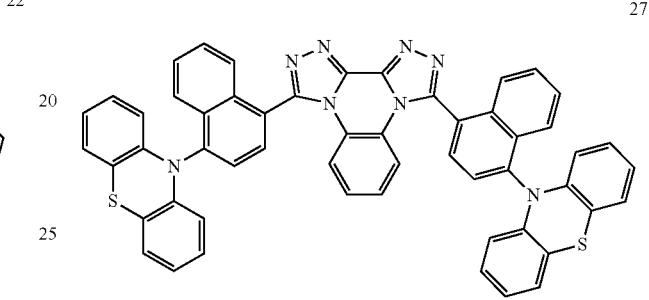
28
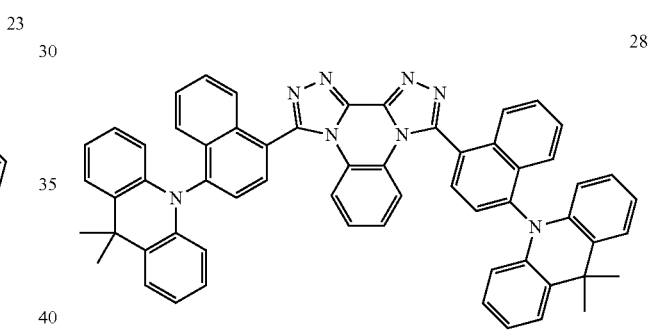
29
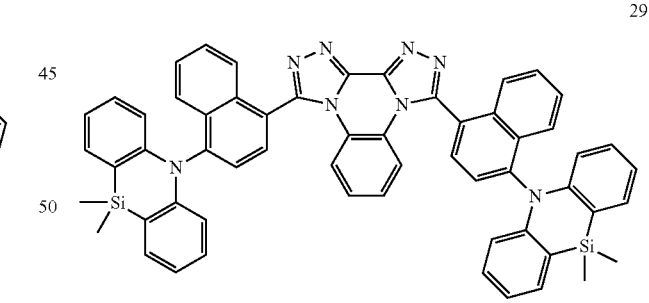
30
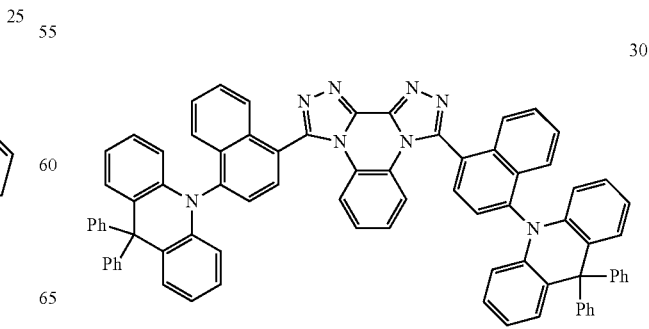

-continued

31

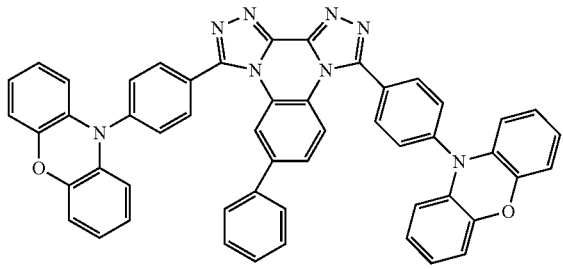

32

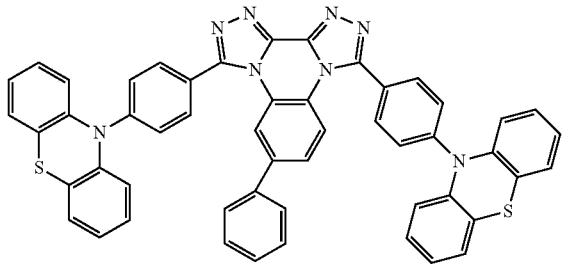

33

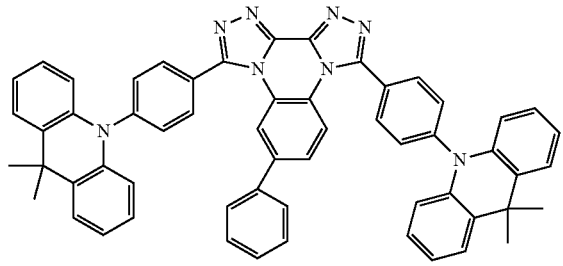

34

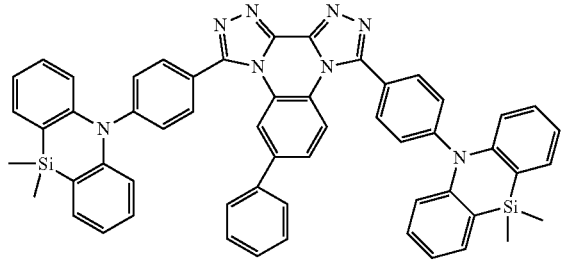

35

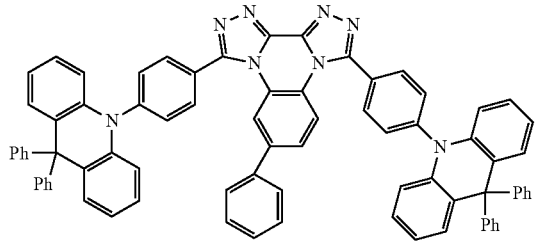

In one embodiment, the energy difference between the lowest singlet excited state (S₁) and the lowest triplet excited state (T₁) in the disclosed compounds may be configured to be $\Delta E_{st} \leq 0.30$ eV.

In another embodiment, the energy difference between the lowest singlet excited state (S₁) and the lowest triplet excited state (T₁) in the disclosed compounds may be configured to be $\Delta E_{st} \leq 0.25$ eV.

In another embodiment, the energy difference between the lowest singlet excited state (S₁) and the lowest triplet excited state (T₁) in the disclosed compounds may be configured to be $\Delta E_{st} \leq 0.20$ eV.

In another embodiment, the energy difference between the lowest singlet excited state (S₁) and the lowest triplet excited state (T₁) in the disclosed compounds may be configured to be $\Delta E_{st} \leq 0.15$ eV.

In another embodiment, the energy difference between the lowest singlet excited state (S₁) and the lowest triplet excited state (T₁) in the disclosed compounds may be configured to be $\Delta E_{st} \leq 0.10$ eV.

In another embodiment, the energy difference between the lowest singlet excited state (S₁) and the lowest triplet excited state (T₁) in the disclosed compounds may be configured to be $\Delta E_{st} \leq 0.05$ eV.

In another embodiment, the energy difference between the lowest singlet excited state (St) and the lowest triplet excited state (T₁) in the disclosed compounds may be configured to be $\Delta E_{st} \leq 0.02$ eV.

In another embodiment, the energy difference between the lowest singlet excited state (S₁) and the lowest triplet excited state (T₁) in the disclosed compounds may be configured to be $\Delta E_{st} \leq 0.01$ eV.

In the disclosed compounds, the energy difference between the lowest singlet excited state (S₁) and the lowest triplet excited state (T₁) may be configured to be $\Delta E_{st} = E_{S1} - E_{T1} \leq 0.30$ eV, or even less than or equal to 0.02 eV, such that the disclosed compounds may exhibit a heat activated delayed fluorescence (TADF) material luminescence mechanism. Thus, the disclosed compounds may be used as TADF materials for the organic optoelectronic devices to improve the luminous efficiency. Moreover, the disclosed compounds may not contain expensive metal complexes, thereby reducing the manufacturing cost and widening the applications.

The present discourse also provides an organic optoelectronic device. The organic optoelectronic device may include an OLED, an organic solar cell, an organic photoelectric sensor, an organic storage device and any other appropriate organic optoelectronic devices. In one embodiment, the organic optoelectronic device may be an OLED. The OLED may include an anode, a cathode, and one or more organic thin film layers disposed between the anode and the cathode. At least one of the organic thin film layers may be a light-emitting layer, and the light-emitting layer may comprise any of the disclosed compounds provided by the present disclosure. The disclosed compound may be used as a dopant material, a co-doping material, or a host material in the light-emitting layer.

In certain embodiments, the OLED may also include at least one or a combination of at least two of a hole transport layer (HTL), a hole injection layer (HIL), an electron blocking layer (EBL), a hole blocking layer (HBL), an electron transport layer (ETL), an electron injection layer (EIL). At least one of the hole transport layer (HTL), the hole injection layer (HIL), the electron blocking layer (EBL), the hole blocking layer (HBL), the electron transport layer (ETL), the electron injection layer (EIL) may comprise any of the disclosed compounds, in which the disclosed compound may be used as a dopant material, a co-doping material, or a host material.

FIG. 1 illustrates a schematic diagram of an exemplary OLED consistent with disclosed embodiments. As shown in FIG. 1, the OLED may include an anode 110 and a cathode 120 disposed on a substrate layer 100. At least a light-emitting layer 130 may be disposed between the anode 110 and the cathode 120. Other appropriate components may also be included. Electrons and holes may be recombined in the light-emitting layer 130, such that light is emitted from light-emitting layer 130.

Figure 2:
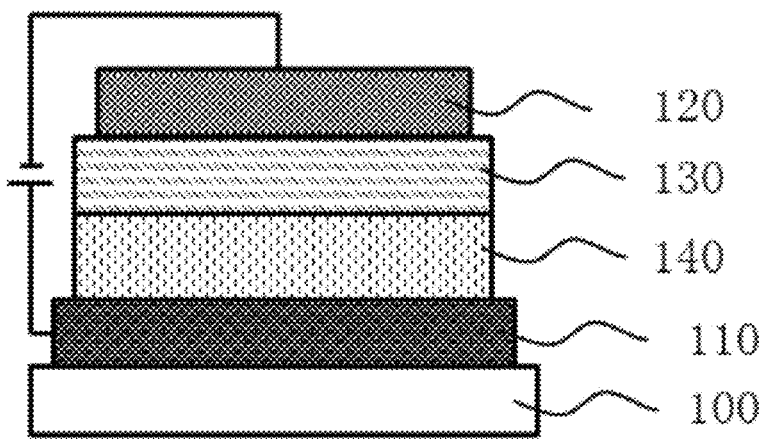
FIG. 2 illustrates a schematic diagram of another exemplary OLED consistent with disclosed embodiments.

FIG. 2 illustrates a schematic diagram of another exemplary OLED consistent with disclosed embodiments. The similarities between FIG. 1 and FIG. 2 are not repeated here, while certain difference may be explained. As shown in FIG. 2, a hole transport layer (HTL) 140 and a light-emitting layer 130 may be disposed between the anode 110 and the cathode 120. The hole transport layer (HTL) 140 may transfer the holes to the light-emitting layer 130.

Figure 3:
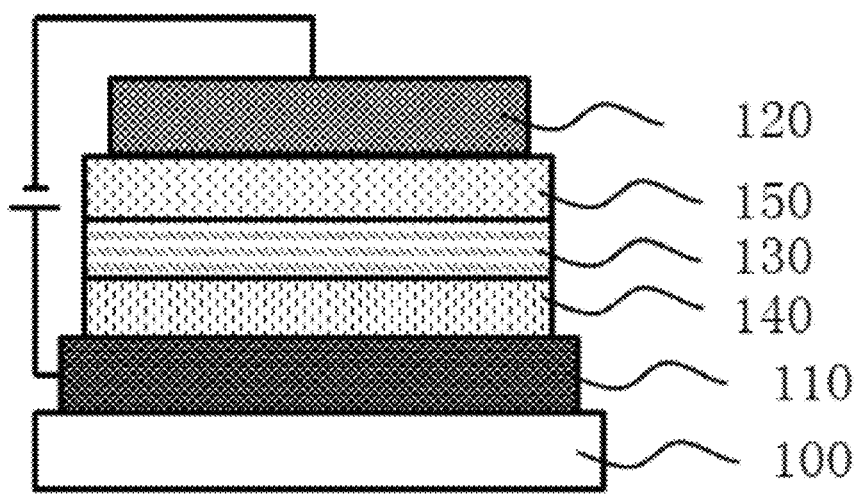
FIG. 3 illustrates a schematic diagram of another exemplary OLED consistent with disclosed embodiments.

FIG. 3 illustrates a schematic diagram of another exemplary OLED consistent with disclosed embodiments. The similarities between FIG. 1 and FIG. 3 are not repeated here, while certain difference may be explained. As shown in FIG. 3, a hole transport layer (HTL) 140, a light-emitting layer 130 and an electron transport layer (ETL) 150 may be disposed between the anode 110 and the cathode 120. The electron transport layer (ETL) 150 may transfer the electrons to the light-emitting layer 130.

Figure 4:
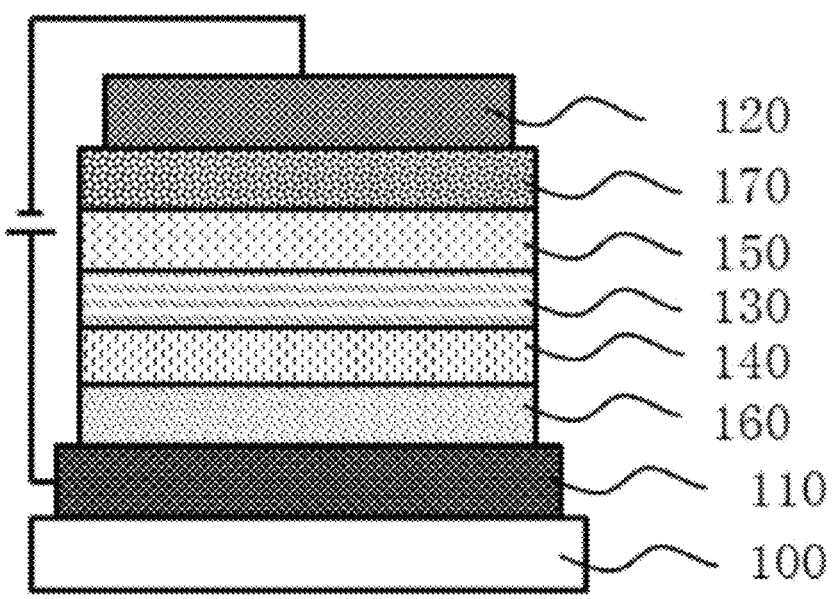
FIG. 4 illustrates a schematic diagram of another exemplary OLED consistent with disclosed embodiments.

FIG. 4 illustrates a schematic diagram of another exemplary OLED consistent with disclosed embodiments. The similarities between FIG. 1 and FIG. 4 are not repeated here, while certain difference may be explained. As shown in FIG. 4, a hole injection layer (HIL) 160, a hole transport layer (HTL) 140, a light-emitting layer 130, an electron transport layer (ETL) 150, and an electron injection layer (EIL) 170 may be disposed between the anode 110 and the cathode 120. The hole injection layer (HIL) 160 may improve the ability to transfer holes from the anode to the organic thin film layers. The electron injection layer (EIL) 170 may improve the ability to transfer electrons from the cathode to the organic thin film layers to reduce the driving voltage of the OLED.

Figure 5:
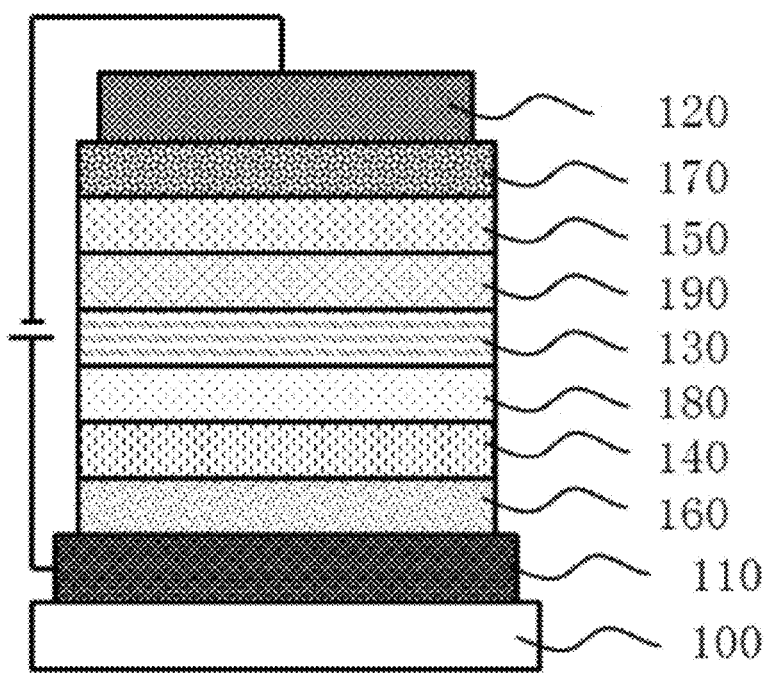
FIG. 5 illustrates a schematic diagram of another exemplary OLED consistent with disclosed embodiments.

FIG. 5 illustrates a schematic diagram of another exemplary OLED consistent with disclosed embodiments. The similarities between FIG. 1 and FIG. 5 are not repeated here, while certain difference may be explained. As shown in FIG. 5, a hole injection layer (HIL) 160, a hole transport layer (HTL) 140, an electron blocking layer (EBL) 180, a light-emitting layer 130, a hole blocking layer (HBL) 190, an electron transport layer (ETL) 150, and an electron injection layer (EIL) 170 may be disposed between the anode 110 and the cathode 120.

Materials of the anode, the cathode, and one or more organic thin film layers disposed between the anode and the cathode will be explained in detail, which are for illustrative purposes and are not intended to limit the scope of the present disclosure.

The anode 110 may be formed by an electrode material having a substantially large work function. The anode 110 may be formed by metals or mixtures of, for example, copper, gold, silver, iron, chromium, nickel, manganese, palladium, platinum. The anode 110 may be formed by metal alloys, for example, copper, gold, silver, iron, chromium, nickel, manganese, palladium or platinum. The anode 110 may be formed by metal oxides or mixture of, for example, indium oxide, zinc oxide, indium tin oxide (ITO), indium zinc oxide (IZO). The anode 110 may be formed by the conductive polymers or mixtures of, for example, polyaniline, polypyrrole, poly (3-methylthiophene). In the disclosed embodiments, the anode may be formed by indium tin oxide (ITO).

The cathode 120 may be formed by an electrode material having a low work function. The cathode 120 may be formed by metals or mixtures of, for example, aluminum, magnesium, silver, indium, tin, titanium, calcium, sodium, potassium, lithium, ytterbium, lead. The cathode 120 may also be formed by multi-layer metal materials, such as LiF/Al, Liq (8-hydroxyquinoline)/Al or a mixture thereof. In the disclosed embodiments, the cathode 120 may be formed by a magnesium silver alloy or a LiF/Al double layer material.

The hole injecting layer (HIL) 160 may be formed by a material, which may facilitate the hole injection at the interface between the anode and the organic film layer and, meanwhile, may be well bonded to the surface of the ITO anode. The material forming the hole injecting layer (HIL) 160 may include, for example, copper phthalocyanine (CuPc) polyporphyrin compounds such as 4,4', 4"-tri-N-naphthyl-N-anilino-triphenylamine (TNATA), poly (3,4-ethylenedioxythiophene): polystyrene sulfonate (PEDOT: PSS) having an HOMO level matching the work function of ITO, 2,3,6,7,10,11-hexacyanoyl-1,4,5,8,9,12-hexaazabenzophenanthrene (HATCN), electron-withdrawing N-heterocyclic compounds such as 2,3,6,7,10,11-hexacyanoyl-1,4,5, 8,9,12-hexaazabenzophenanthrene (HATCN).

The hole transport layer (HTL) 140 and the electron blocking layer (EBL) 180 may be formed by a material having a high glass transition temperature and a high hole mobility. Materials used as the hole transport layer (HTL) 140 and the electron blocking layer (EBL) 180 may include biphenyl diamine derivatives such as diphenylnaphthylene-diamine (NPD), crosslinked diamine biphenyl derivatives such as 2,2', 7,7'-tetrakis (diphenylamino)-9,9'-spirobifluorene (spiro-TAD), stellate triphenylamine derivatives such as 4',4"-tris (N-carbazolyl) triphenylamine (TCTA).

The hole blocking layer (HBL) 190 and the electron transport layer (ETL) 150 may be formed by a material having a low HOMO level and high electron mobility. Materials used as the hole blocking layer and the electron transport layer may include quinoline metal complexes such as bis (8-hydroxy-2-methylquinoline)-diphenol aluminum (BAlq), tris (8-quinolinolato) aluminum (Alq), 8-hydroxyquinoline lithium, phenanthroline derivatives such as 4,7-diphenyl-1,10-phenanthroline (Bphen), imidazole derivatives such as 1,3,5,3-tris (N-phenyl-benzimidazol-2-yl) benzene (TPBI), and triazine derivatives such as 2,4,6-tricarbazolyl-1,3,5-triazine.

Figure 6:
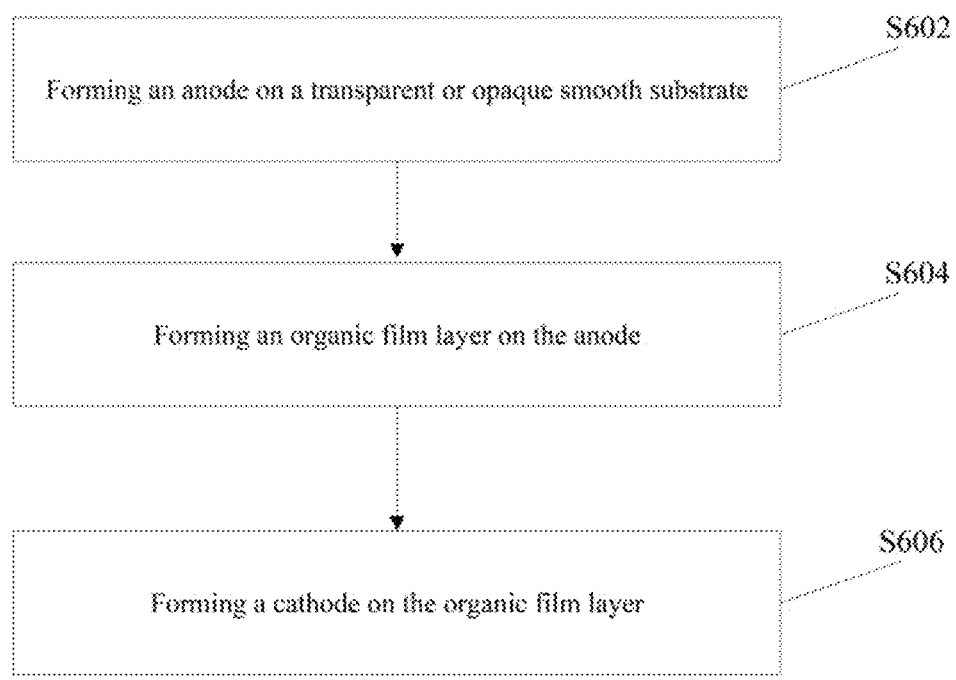
FIG. 6 illustrates a flow chart of an exemplary OLED fabrication method consistent with disclosed embodiments.

FIG. 6 illustrates a flow chart of an exemplary OLED fabrication method consistent with disclosed embodiments. As shown in FIG. 6, the OLED may be fabricated by forming an anode on a transparent or opaque smooth substrate (S602), forming an organic film layer on the anode (S604), and forming a cathode on the organic film layer (S606). The organic film layer may be formed by an existing method, such as vapor deposition, sputtering, spin coating, dipping, or ion plating.

The preparation of the certain disclosed Compounds will be explained as follows, which is for illustrative purposes and is not intended to limit the scope of the present disclosure. The disclosed compounds may be prepared in other appropriate methods.

Example 1: Preparation of Compound 3

Compound 3

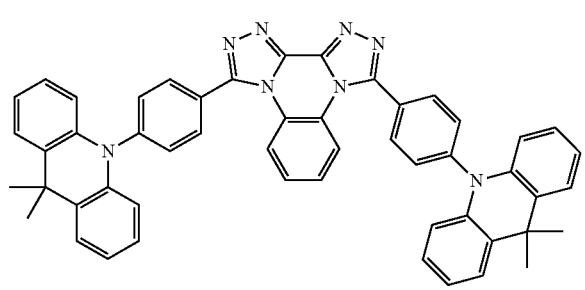 [SMILES: CC1(C)c2ccccc2N(c2ccc(-c3nnc4c5nnc(-c6ccc(N7c8ccccc8C(C)(C)c8ccccc87)cc6)n5c5ccccc5n34)cc2)c2ccccc21]

may be prepared through the following chemical reaction:

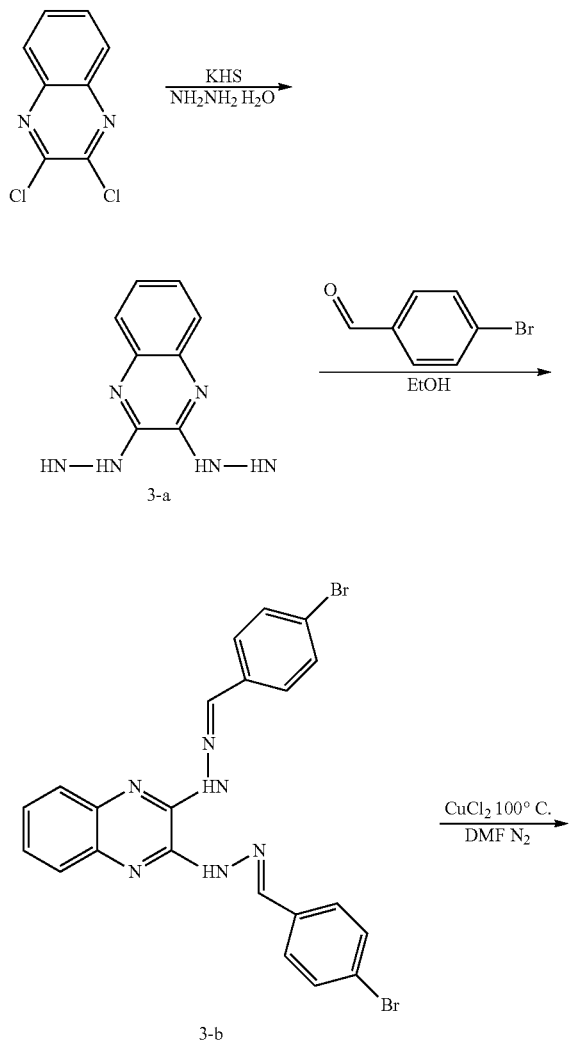

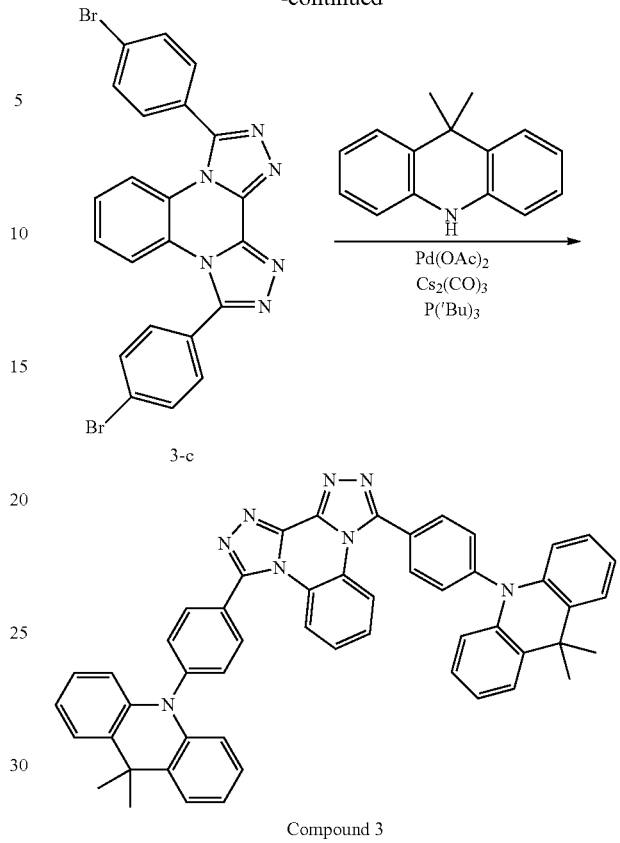

Compound 3

In particular, in the first step, to prepare the intermediate (3-a), a solution of 2,3-dichloroquinoxaline (7.92 g, 40 mmol) and potassium thiocyanate (0.25 g, 3.4 mol) was dissolved in 50 mL of aqueous solution of hydrazine, and reacted in an ice bath for 5 hours under a nitrogen atmosphere. The reaction solution was washed successively with water and saturated brine, dried, and purified by silica gel column chromatography. Then solid compounds 3-a (5.27 g, 28 mmol) was obtained. The yield was about 70% yield, and ESI-MS (m/z) obtained by liquid phase mass spectrometry was about 188.1.

In the second step, to prepared the intermediate (3-b), the intermediate (3-a) (3.76 g, 20 mmol) and 4-bromobenzaldehyde (9.20 g, 50 mmol) were dissolved in ethanol and refluxed for 5 hours. The ethanol was dried under vacuum, and the solid was dissolved in ethyl acetate. The mixture was stirred, filtered, washed with saturated brine three times, and the solvent was evaporated under vacuum and purified by silica gel column chromatography. Solid compound 3-b (5.76 g, 11 mmol) was obtained. The yield was about 55%, and ESI-MS (m/z) obtained by liquid phase mass spectrometry was about 524.

In the third step, to prepared the intermediate (3-c), the intermediate (3-b) (9.48 g, 18.1 mmol) and copper chloride (1.3 g, 18 mmol) were dissolved in 50 mL of N, N-dimethylformamide solution, and reacted in an ice bath for 5 hours under a nitrogen atmosphere. The reaction solution was washed successively with water and saturated brine, dried, and purified by silica gel column chromatography. Solid compound 3-c (6.5 g, 12.5 mmol) was obtained. The yield was about 69%, and ESI-MS (m/z) obtained by liquid phase mass spectrometry was about 519.9.

After the intermediate (3-c) was prepared, Compound 3 may be obtained as follows. In the fourth step, the intermediate (3-c) (8.32 g, 16 mmol), 9,9-dimethylacridine (7.59 g, 36.30 mmol), palladium acetate (0.4 g, 1.98 mmol), cesium carbonate (11.5 g, 33 mmol) and tert-(0.5 g, 2.4 mmol) were dissolved in toluene, refluxed and stirred for 5 hours. The toluene was dried under vacuum and the solid was dissolved in ethyl acetate. The mixture was stirred, filtered, and washed with saturated brine three times. The solvent was evaporated in a vacuum steam machine. After being purified by silica gel column chromatography, solid Compound 3 (8.38 g, 10.8 mmol) was obtained. The yield was about 67.5%, and ESI-MS (m/z) obtained by liquid phase mass spectrometry was about 776.3.

The synthesis of Compounds 1, 2, 4, 5 may be similar to that of Compound 3, except that in the step to prepare Compounds 1, 2, 4, 5 based on the intermediate (3-c), 9,9-dimethylacridine was replaced by 10 hydrogen-phenoxazine, 10 hydrogen-phenothiazine, 10,10-dimethyl-5-hydro-phenylene silane, 9,9-diphenylacridine, respectively.

Example 2: Preparation of Compound 6

Compound 6 may be prepared through the following chemical:

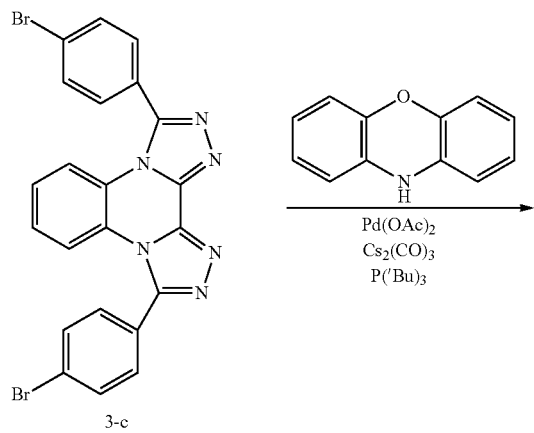

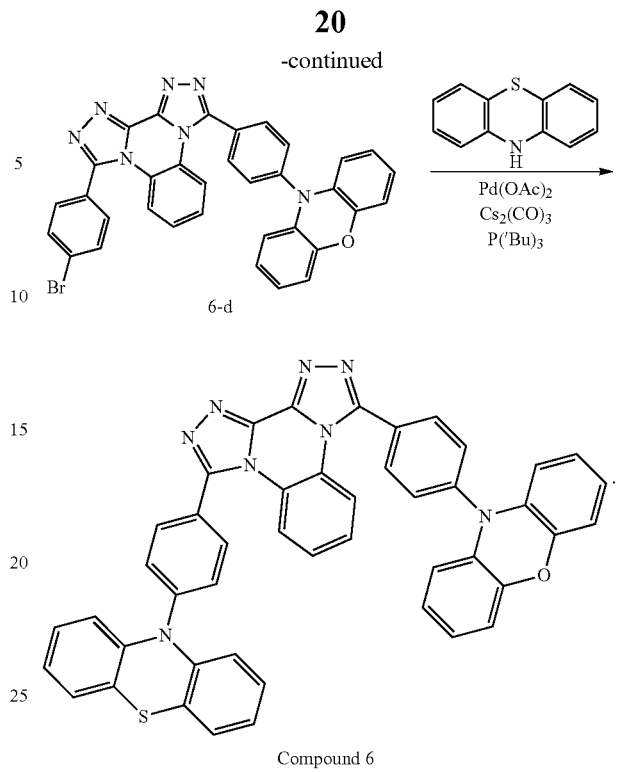

Compound 6

In particular, in the first step, to prepare the intermediate (6-d), the intermediate (3-c) (8.32 g, 16 mmol), 10 hydrogen-phenoxazine (3.02 g, 16.5 mmol), palladium acetate (0.4 g, 1.98 mmol), cesium carbonate (11.5 g, 33 mmol) and t-butylphosphine (0.5 g, 2.4 mmol) were dissolved in toluene, refluxed and stirred for 5 hours. The toluene was dried under volume and the solid was dissolved in ethyl acetate. The mixture was stirred, filtered and washed three times with saturated brine. The solvent was evaporated in a vacuum steam machine. After being purified by silica gel column chromatography, solid compound 6-d (4.24 g, 6.8 mmol) was obtained. The yield was about 42.5%, and ESI-MS (m/z) obtained by liquid phase mass spectrometry was about 623.1.

After the intermediate (6-d) was prepared, Compound 6 may be obtained as follows. In the second step, the intermediate (6-d) (9.97 g, 16 mmol), 10 hydrogen-phenothiazine (3.38 g, 17 mmol), palladium acetate (0.4 g, 1.98 mmol), cesium carbonate (11.5 g, 33 mmol) and t-butylphosphine (0.5 g, 2.4 mmol) were dissolved in toluene, refluxed and stirred for 5 hours. The toluene was dried under vacuum and the solid was dissolved in ethyl acetate. The mixture was stirred, filtered and washed three times with saturated brine. The solvent was evaporated in a vacuum steam machine. After being purified by silica gel column chromatography, solid Compound 6 (7.5, 10.1 mmol) was obtained. The yield was about 63%, and ESI-MS (m/z) obtained by liquid phase mass spectrometry was about 740.2.

Compounds 7-15 may be synthesized in a similar manner as Compound 6 according to the desired structure, except that in the first and second steps of preparing Compound 6,10 hydrogen-phenoxazine, 9,9-dimethylacridine, 10-hydro-6,10-dimethyl-5-hydro-phenylene silane, 9,9-diphenylacridine was adopted.

Example 3: Preparation of Compound 21

Compound 21

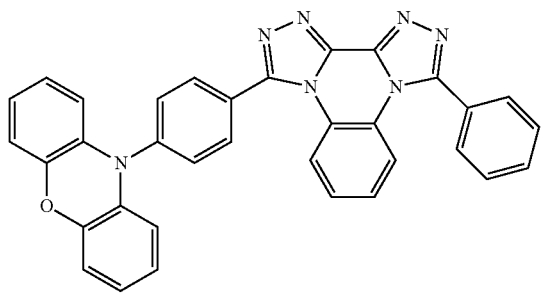

may be prepared through the following chemical reaction:

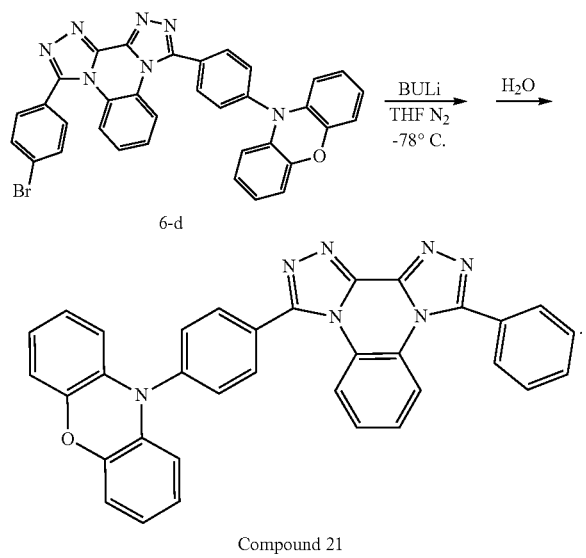

In particular, in the first step, to prepare Compound 21, the intermediate (6-d) (6.97 g, 16 mmol) was dissolved in 50 mL of tetrahydrofuran solution, and butyllithium (1.1 g, 17 mmol) was also slowly added under nitrogen and ice-salt bath. After reacted for 2 hours, 20 ml of water was slowly added to the reaction mixture, then the reaction mixture was washed successively with water and saturated brine. After being purified by silica gel column chromatography, solid Compound 21 (7.06 g, 13 mmol) was obtained. The yield was about 88%, and ESI-MS (m/z) obtained by liquid phase mass spectrometry was about 543.2.

Compounds 21-25 may be synthesized in a similar manner as Compound 21, except that in the first step of preparing the Compound 21, 10 hydro-phenoxazine was replaced by 10 hydrogen-phenothiazine, 9,9-dimethylacridine, 10,10-dimethyl-5-hydro-phenylene silane, 9,9-diphenylacridine, respectively.

Compound 28 may be synthesized in a similar manner as the Compound 3, except that in the second step of preparing the Compound 3, 4-bromobenzaldehyde was replaced by 1-bromo-4-naphthaldehyde.

Compounds 26, 27, 29, 30 may be synthesized in a similar manner as Compound 28, except that in the fourth step of preparing the Compound 28, 9,9-dimethylacridine was replaced by 10-hydrophenazine, 10-hydro-phenothiazine, 10,10-dimethyl-5-hydro-phenylene silane, 9,9-diphenylacridine, respectively.

Compound 33 may be synthesized in a similar manner as the Compound 3, except that in the first step of preparing the Compound 3, 2,3-dichloroquinoxaline was replaced by 2,3-dichloro-7-phenylquinoxaline.

Compounds 31, 32, 34, and 35 may be synthesized in a similar manner as the Compound 33, except that in the fourth step of preparing the Compound 33, 9,9-dimethylacridine was replaced by 10-hydroo-phenoxazine, 10-hydro-phenothiazine, 10-dimethyl-5-hydro-phenylene silane, 9,9-diphenylacridine, respectively.

Example 4: Simulation of Compounds

The energy difference between single and triplet states of the disclosed compounds may be obtained by Guassian 09 software (Guassian Inc.). The energy difference ΔEst may be simulated according to the simulation method described in J. Chem. Theory Comput., 2013 (DOI: 10.1021/ct400415r). The molecular structure optimization and molecular excitation may be performed by using the TD-DFT method "B3LYP" and the base group "6-31g (d)". For illustrative purposes, a simulation is performed for the Compounds 1-3 and 23 selected from the compounds 1-35. The simulation results of the Compounds 1-3 and 23 are shown in Table 1.

TABLE 1

Simulation results of four exemplary compounds

| Compound | $S_1$(eV) | $T_1$(eV) | $\Delta E_{st}$(eV) |
|---|---|---|---|
| 3 | 3.01 | 2.94 | 0.07 |
| 1 | 2.75 | 2.69 | 0.06 |
| 2 | 3.10 | 2.86 | 0.24 |
| 23 | 3.03 | 2.95 | 0.08 |

As shown in Table 1, the energy difference between single and triplet states of disclosed compounds are substantially small, which may enable efficient reverse intersystem crossing (RISC) in the compounds and provide TADF properties. Thus, the disclosed compounds may have a heat activated delayed fluorescence (TADF) material luminescence mechanism, which may be used as a new type of TADF material in the organic optoelectronic devices to improve the luminous efficiency. Moreover, the disclosed compounds may be prepared without expensive metal complexes, thereby reducing the manufacturing cost and widening the applications.

Example 5: Organic Optoelectronic Device Fabrication and Testing

Figure 7:
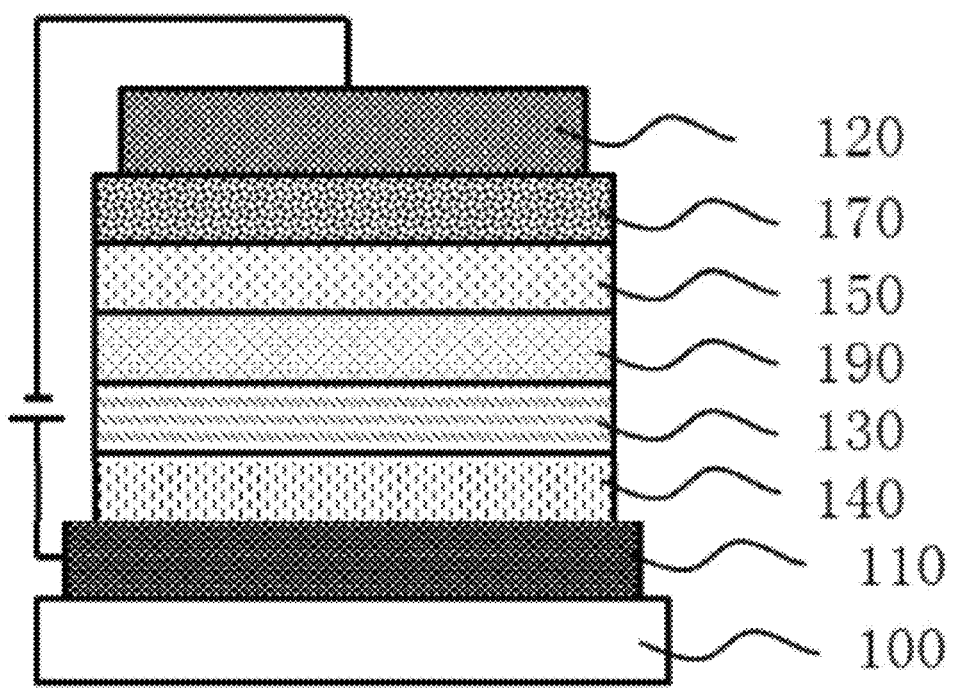
FIG. 7 illustrates a schematic diagram of another exemplary OLED consistent with disclosed embodiments.

To evaluate the performance of the disclosed organic optoelectronic devices, six exemplary organic optoelectronic devices (named as 1st disclosed organic optoelectronic device to the 8th disclosed organic optoelectronic device), and two reference organic optoelectronic devices (named as 1st reference organic optoelectronic device and the 2nd reference organic optoelectronic device) were fabricated. The 1st to the 8th disclosed organic optoelectronic devices and the 1st to the 2nd reference organic optoelectronic devices have the same structure shown in FIG. 7, except that the materials for forming various layers are different.

To fabricate the 1st disclosed organic optoelectronic device, a substrate coated with a 100-nm-thick ITO film as the anode 110 was ultrasonically cleaned with distilled water, acetone, isopropanol, then dried in an oven, treated with UV for 30 minutes, and transferred to a vacuum evaporation chamber. Various organic films were vapor-deposited under a vacuum of 2×10−6 Pa. 60-nm-thick diphenylnaphthalenediamine (NPD) film and 10-nm-thick 4,4',4''-tris (N-carbazolyl) triphenylamine (TCTA) film were vapor-deposited on the anode 110 to form a hole transport layer (HTL) 140. 6 wt % Ir (ppy)$_3$ was used as the green phosphorescent dopant material and 94 wt % Compound 3 was used as the host material, which were vapor-deposited on the hole transport layer (HTL) 140 to form a 30-nm-thick light-emitting layer 130.

Then, bis (8-hydroxy-2-methylquinoline)-diphenol aluminum (BAlq) was vapor-deposited on the light-emitting layer 130 to form a 5-nm-thick hole blocking layer (HBL) 190. 4,7-diphenyl-1,10-phenanthroline (Bphen) was vapor-deposited on the hole blocking layer (HBL) 190 to form a 20-nm-thick electron transport layer (ETL) 150. 1-nm-thick LiF and 100-nm-thick Al were successively deposited as an electron injection layer (EIL) 170 and the cathode 120 on the electron transport layer (ETL) 150, respectively.

The fabricated 1$^{st}$ disclosed organic optoelectronic device has a structure of ITO (100 nm)/NPD (60 nm)/TCTA (10 nm)/Ir (ppy)$_3$: Compound 3 (6 wt %: 94 wt %, 30 nm)/BAlq (5 nm)/Bphen (20 nm)/LiF (1 nm)/Al (100 nm).

The 2$^{nd}$ disclosed organic optoelectronic device was fabricated in the same manner as 1$^{st}$ disclosed organic optoelectronic device, except that Compound 1 was adopted instead of Compound 3 as the host material in the 2$^{nd}$ disclosed organic optoelectronic device.

The 3$^{rd}$ disclosed organic optoelectronic device was fabricated in the same manner as 1$^{st}$ disclosed organic optoelectronic device, except that Compound 2 was adopted instead of Compound 3 as the host material in the 3$^{rd}$ disclosed organic optoelectronic device.

The 4$^{th}$ disclosed organic optoelectronic device was fabricated in the same manner as 1$^{st}$ disclosed organic optoelectronic device, except that Compound 23 was adopted instead of Compound 3 as the host material in the 4$^{th}$ disclosed organic optoelectronic device.

The 1$^{st}$ reference organic optoelectronic device was fabricated in the same manner as 1$^{st}$ disclosed organic optoelectronic device, except that 6 wt % Ir (ppy)$_3$ was adopted as the dopant material, and 94 wt % CBP was adopted as the host material, which were vapor-deposited on the hole transport layer (HTL) 140 to form a 30-nm-thick light-emitting layer 130.

The 5$^{th}$ disclosed organic optoelectronic device was fabricated in the same manner as 1$^{st}$ disclosed organic optoelectronic device, except that 5 wt % Compound 1 was adopted as the dopant material, and 95 wt % DPEPO was adopted as the host material, which were vapor-deposited on the hole transport layer (HTL) 140 to form a 30-nm-thick light-emitting layer 130.

The fabricated 5$^{th}$ disclosed organic optoelectronic device has a structure of ITO (100 nm)/NPD (60 nm)/TCTA (10 nm)/Compound 1: DPEPO (5 wt %: 95 wt %, 30 nm)/BAlq (5 nm)/Bphen (20 nm)/LiF (1 nm)/Al (100 nm).

The 6$^{th}$ disclosed organic optoelectronic device was fabricated in the same manner as 5$^{th}$ disclosed organic optoelectronic device, except that Compound 2 was adopted instead of Compound 1 as the dopant material in the 6$^{th}$ disclosed organic optoelectronic device.

The 7$^{th}$ disclosed organic optoelectronic device was fabricated in the same manner as 5$^{th}$ disclosed organic optoelectronic device, except that Compound 3 was adopted instead of Compound 1 as the dopant material in the 7$^{th}$ disclosed organic optoelectronic device.

The 8$^{th}$ disclosed organic optoelectronic device was fabricated in the same manner as 5$^{th}$ disclosed organic optoelectronic device, except that Compound 23 was adopted instead of Compound 1 as the dopant material in the 8$^{th}$ disclosed organic optoelectronic device.

The 2$^{nd}$ reference organic optoelectronic device was fabricated in the same manner as 5$^{th}$ disclosed organic optoelectronic device, except that 5 wt % DPAVB was adopted as the dopant material, and 95 wt % DPEPO was adopted as the host material, which were vapor-deposited on the hole transport layer (HTL) 140 to form a 30-nm-thick light-emitting layer 130.

The chemical formulas of DPAVB, DPEPO, Ir(ppy)$_3$, BAlq, Bphen, a-NPD, TCTA, and CBP are shown below.

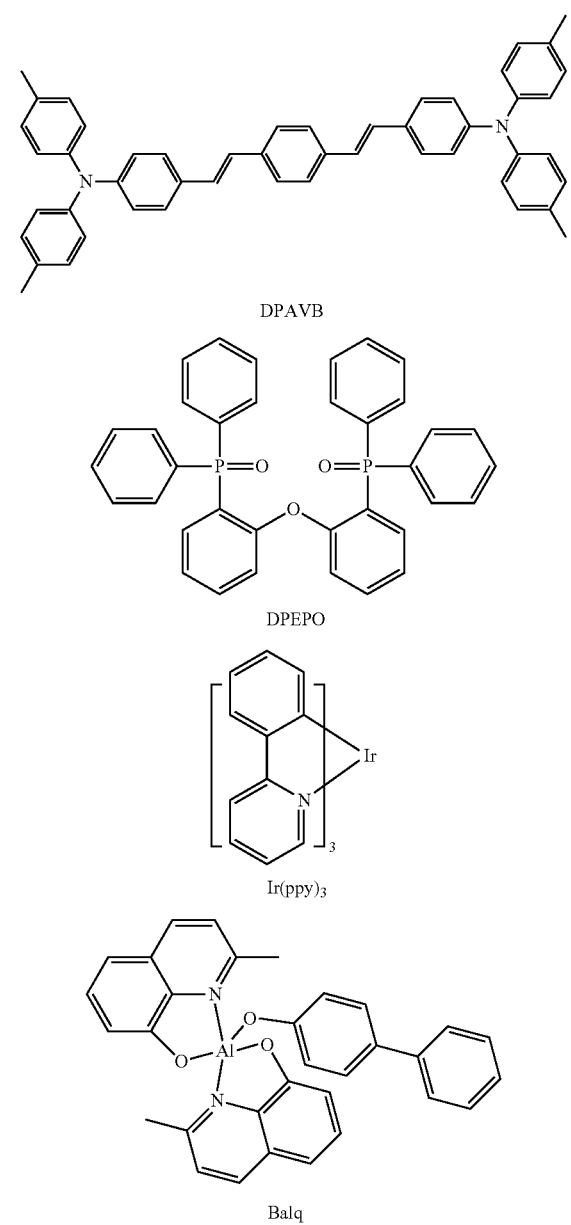

DPAVB

DPEPO

Ir(ppy)$_3$

Balq

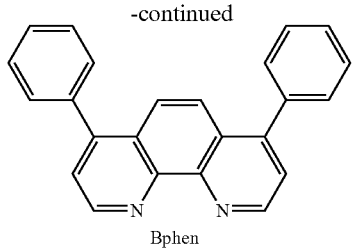

Bphen

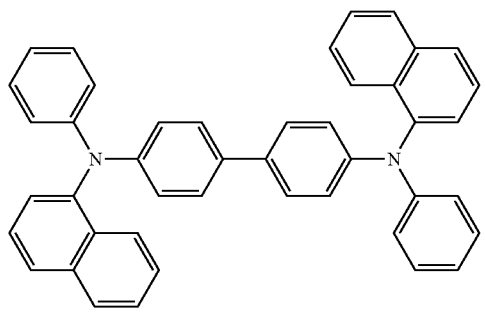

a-NPD

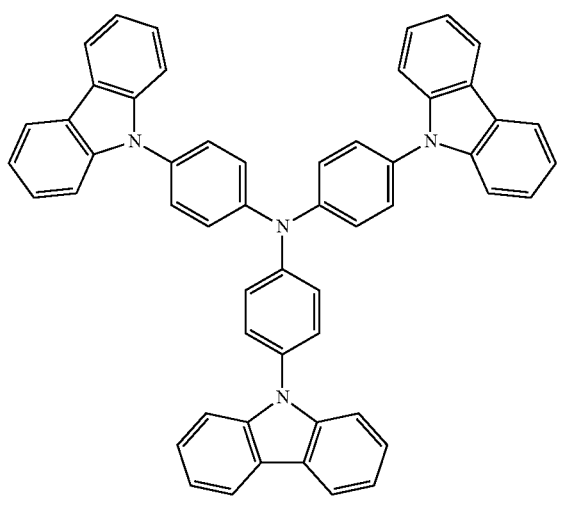

TCTA

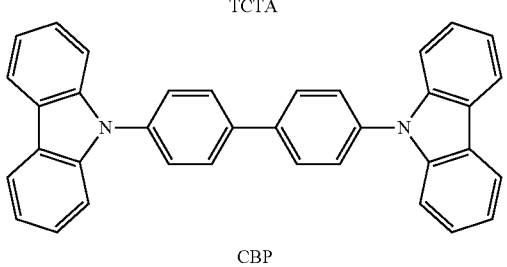

CBP

The current of the 1$^{st}$ to 6$^{th}$ disclosed organic optoelectronic devices and the 1$^{st}$ to 2$^{nd}$ reference organic optoelectronic devices under different voltages was measure by Keithley 2365A digital nanovolt meter, respectively. Then the corresponding current density was calculated by dividing the current by the light-emitting area. The luminance and radiant energy density of the 1$^{st}$ to 6$^{th}$ disclosed organic optoelectronic devices and the 1$^{st}$ to 2$^{nd}$ reference organic optoelectronic devices under different voltages was measure by Konicaminolta CS-2000 spectrophotometer, respectively. Based on the current density and the luminance under different voltages, the current efficiency (Cd/A) and the external quantum efficiency (EQE) under a given current density (0.1 mA/cm$^2$) was obtained.

The testing results of the 1$^{st}$ to 4$^{th}$ disclosed organic optoelectronic devices in which the disclosed compounds are used as the host material and the 1$^{st}$ reference organic optoelectronic device are shown in the following Table 2.

TABLE 2

Testing results of the 1$^{st}$ to 4$^{th}$ disclosed organic optoelectronic devices and the 1$^{st}$ reference organic optoelectronic device

| | Voltage (V) | Current efficiency (Cd/A) | EQE (%) | Color |
|---|---|---|---|---|
| 1$^{st}$ disclosed organic optoelectronic device | 4.6 | 43.2 | 17.1 | Green |
| 2$^{nd}$ disclosed organic optoelectronic device | 4.7 | 44.0 | 17.2 | Green |
| 3$^{rd}$ disclosed organic optoelectronic device | 4.8 | 41.6 | 16.5 | Green |
| 4$^{th}$ disclosed organic optoelectronic device | 4.8 | 42.7 | 17.0 | Green |
| 1$^{st}$ reference organic optoelectronic device | 5.1 | 40.3 | 15.6 | Green |

The testing results of the 5$^{th}$ to 8$^{th}$ disclosed organic optoelectronic devices in which the disclosed compounds are used as the guest dopant material and the 2$^{nd}$ reference organic optoelectronic device are shown in the following Table 3.

TABLE 3

Testing results of the 5$^{th}$ to 8$^{th}$ disclosed organic optoelectronic devices and the 2$^{nd}$ reference organic optoelectronic device

| | Voltage (V) | Current efficiency (Cd/A) | EQE (%) | Color |
|---|---|---|---|---|
| 5$^{th}$ disclosed organic optoelectronic device | 6.8 | 8.6 | 8.2 | Blue |
| 6$^{th}$ disclosed organic optoelectronic device | 8.4 | 7.9 | 7.8 | Blue |
| 7$^{th}$ disclosed organic optoelectronic device | 7.5 | 8.5 | 8.1 | |
| 8$^{th}$ disclosed organic optoelectronic device | 7.4 | 7.7 | 7.6 | |
| 2$^{nd}$ reference organic optoelectronic device | 8.8 | 5.5 | 4.9 | Blue |

According to the testing results shown in Table 2, under the same current density (0.1 mA/cm$^2$), the 1$^{st}$ to 4$^{th}$ disclosed organic optoelectronic devices have a driving voltage lower than 5V, current efficiency higher than 40 Cd/A, and external quantum efficiency (EQE) largher than 15. That is, the 1st to 4th disclosed organic optoelectronic devices have a lower driving voltage, higher current efficiency and external quantum efficiency (EQE) than the 1st reference organic optoelectronic devices. The testing results shown in Table 2 may indicate that the disclosed compounds may be used as host materials.

According to the testing results shown in Table 3, under the same current density (0.1 mA/cm$^2$), the 5$^{th}$ to 8$^{th}$ disclosed organic optoelectronic devices have a lower driving voltage, higher current efficiency and external quantum efficiency (EQE) than the 2$^{nd}$ reference organic optoelectronic device. The testing results shown in Table 3 may indicate that the disclosed compounds may be used as dopant materials or co-doping materials. According to the testing results shown in Table 2 and Table 3, the optoelectronic device comprising the disclosed compounds may have excellent luminescent properties.

The description of the disclosed embodiments is provided to illustrate the present disclosure to those skilled in the art. Various modifications to these embodiments will be readily apparent to those skilled in the art, and the generic principles defined herein may be applied to other embodiments without departing from the spirit or scope of the disclosure. Thus, the present disclosure is not intended to be limited to the embodiments shown herein but is to be accorded the widest scope consistent with the principles and novel features disclosed herein.

What is claimed is:

1. A compound of the following chemical formula (I):

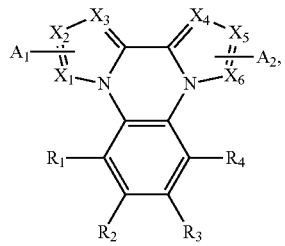

formula (I)

wherein: in the chemical formula (I),

R$_1$ to R$_{10}$ are independently selected from hydrogen, deuterium, C$_1$ to C$_{30}$ alkyl, C$_1$ to C$_{30}$ heteroatom-substituted alkyl, C$_6$ to C$_{30}$ aryl, and C$_2$ to C$_{30}$ heteroaryl, X$_1$ to X$_6$ are independently selected from C and N, when N is selected, N does not include a substituent, and when C is selected, C includes a substituent selected from hydrogen, deuterium, C$_1$ to C$_{30}$ alkyl, C$_1$ to C$_{30}$ heteroatom-substituted alkyl, C$_6$ to C$_{30}$ aryl, and C$_2$ to C$_{30}$ heteroaryl, at least one of X$_1$ to X$_3$ and at least one of X$_4$ to X$_6$ are selected as C and, meanwhile, connected to A$_1$ and A$_2$, respectively, and A$_1$ and A$_2$ are chemical groups independently represented by the following chemical formula (II):

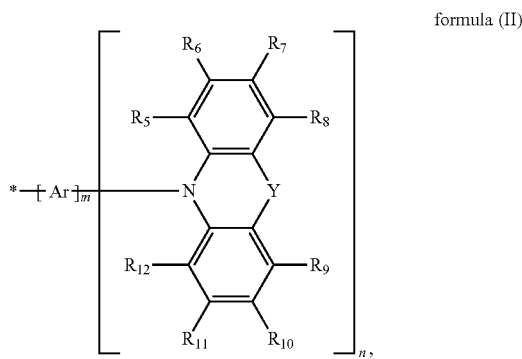

formula (II)

wherein: in the chemical formula (II),

R$_5$ to R$_{12}$ are independently selected from hydrogen, deuterium, C$_1$ to C$_{30}$ alkyl, C$_1$ to C$_{30}$ heteroatom-substituted alkyl, C$_6$ to C$_{30}$ aryl, and C$_2$ to C$_{30}$ heteroaryl, Y is selected from O, S, substituted or unsubstituted imino, substituted or unsubstituted methylene, substituted or unsubstituted silylene, and a substituent is selected from hydrogen, deuterium, C$_1$ to C$_{30}$ alkyl, C$_1$ to C$_{30}$ heteroatom-substituted alkyl, C$_6$ to C$_{30}$ aryl, and C$_2$ to C$_{30}$ heteroaryl, Ar is selected from C$_6$ to C$_{30}$ aryl and C$_2$ to C$_{30}$ heteroaryl, m represents 0 or 1, and n represents 0 or 1, and n in A$_1$ and n in A$_2$ are not zero at the same time.

2. The compound according to claim 1, wherein:

the compound is represented by the following chemical formula (III):

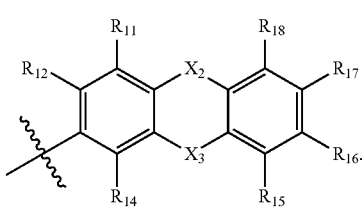

chemical formula (III)

3. The compound according to claim 2, wherein:

Y is selected from 0, S, —C(CH$_3$)$_2$—, —C(Ph)$_2$-, and —Si(CH$_3$)$_2$—.

4. The compound according to claim 1, wherein:

the C$_6$ to C$_{30}$ aryl is selected from phenyl and naphthyl.

5. The compound according to claim 1, wherein:

m in A$_1$ and m in A$_2$ are 1 at the same time; and n in A$_1$ and n in A$_2$ are 1 at the same time.

6. The compound according to claim 1, comprising a compound selected from the following:

1

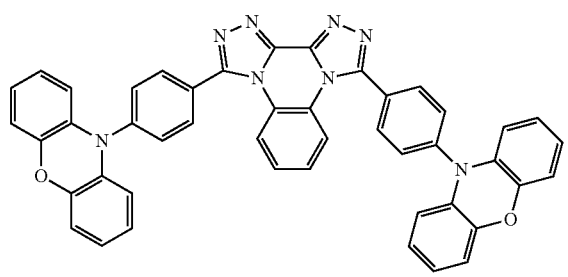

2
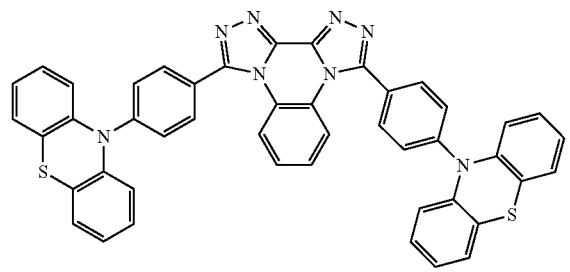 [SMILES: c1ccc2c(c1)Oc1ccccc1N2c1ccc(-c2nnc3c4nnc(-c5ccc(N6c7ccccc7Sc7ccccc76)cc5)n4c4ccccc4n23)cc1]
3
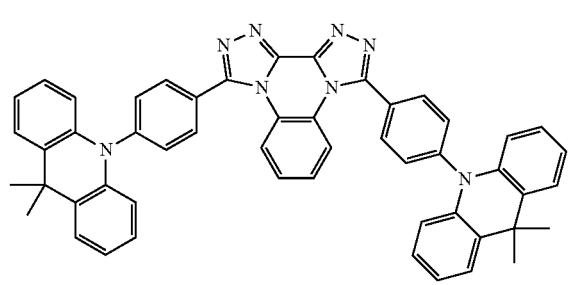
4
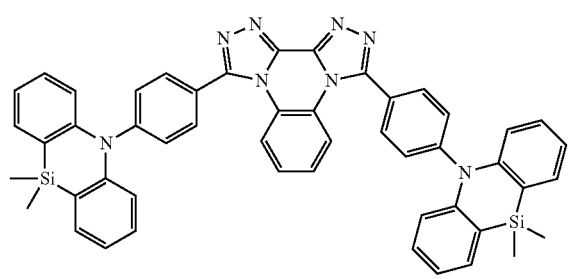
5
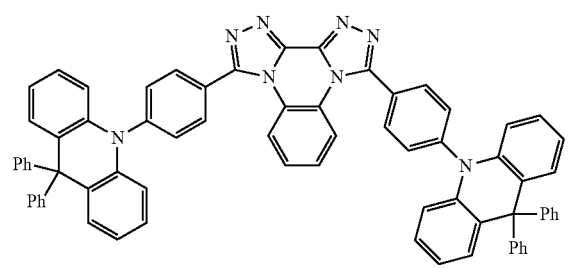
6
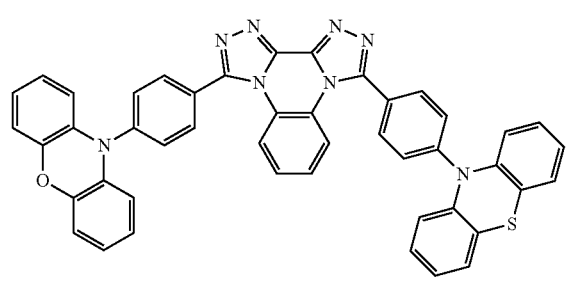
7
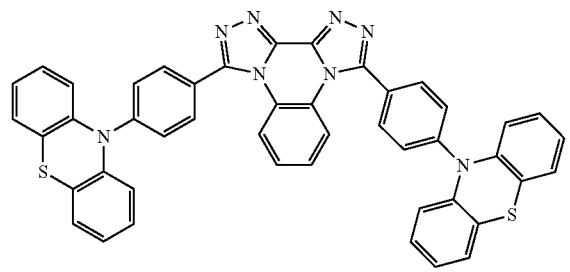 [SMILES: c1ccc2c(c1)Oc1ccccc1N2c1ccc(-c2nnc3c4nnc(-c5ccc(N6c7ccccc7Sc7ccccc76)cc5)n4c4ccccc4n23)cc1]
8
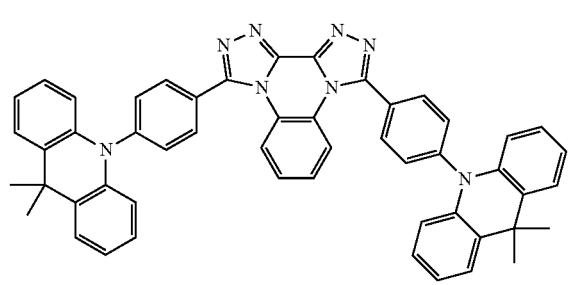
9
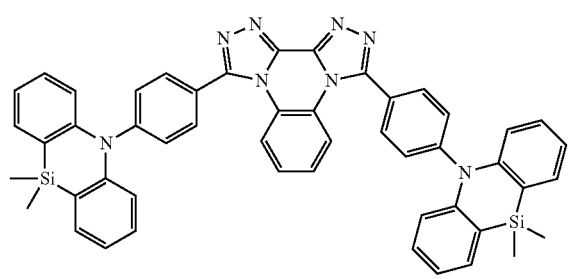
10
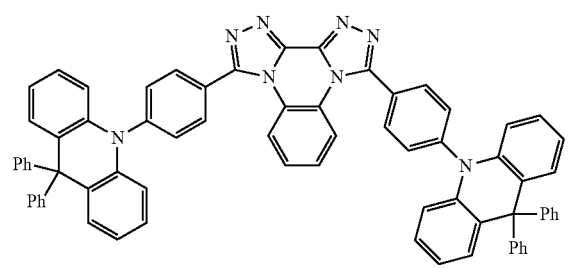
11
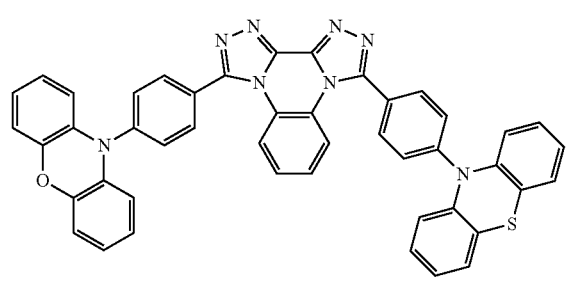

12
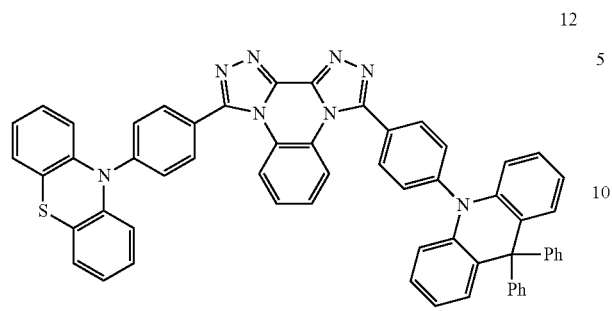
13
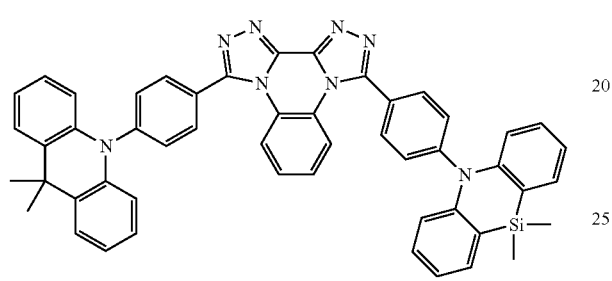
14
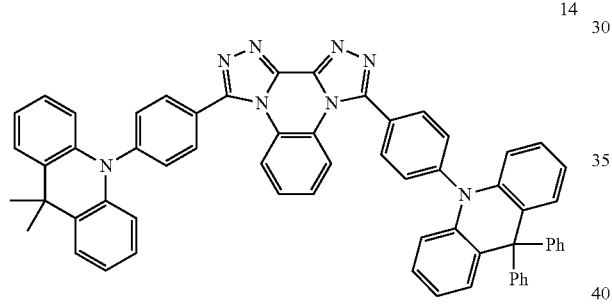
15
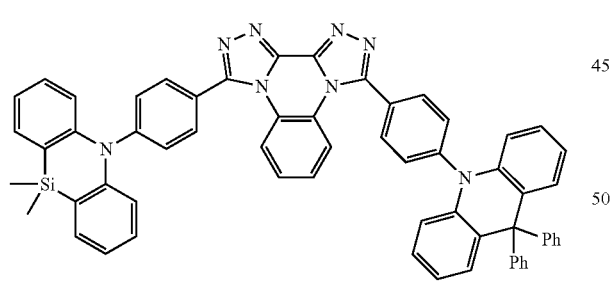
16
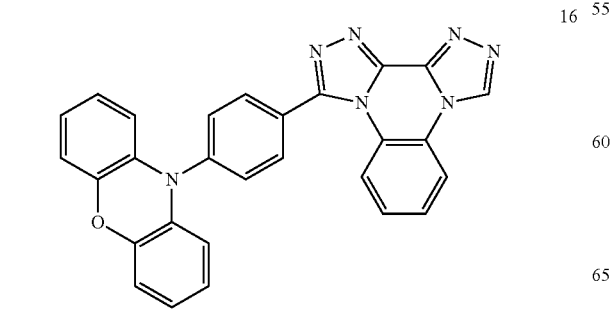
17
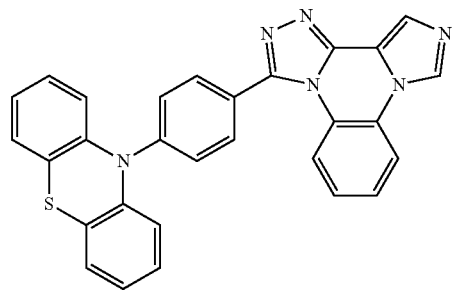
18
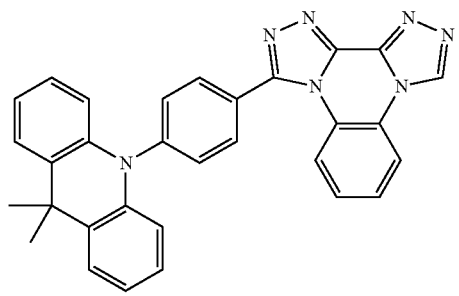
19
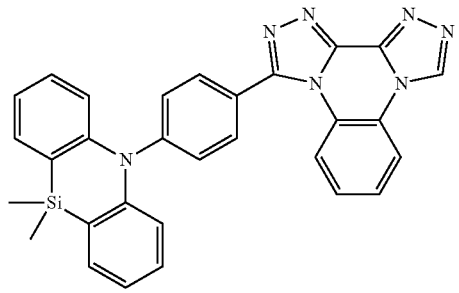
20
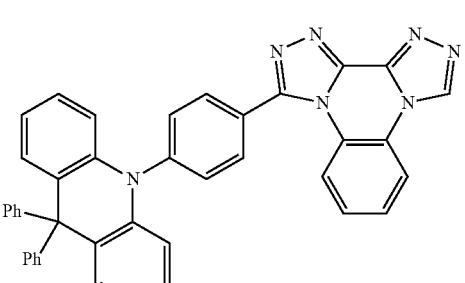
21
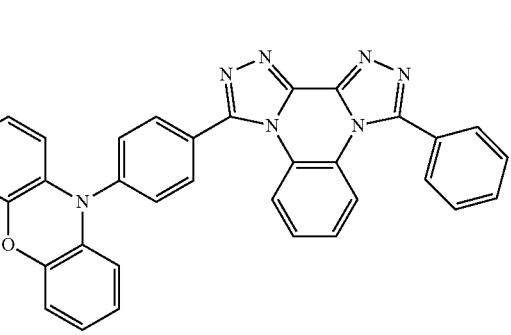

22
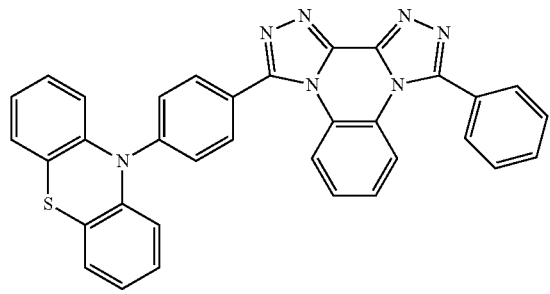
23
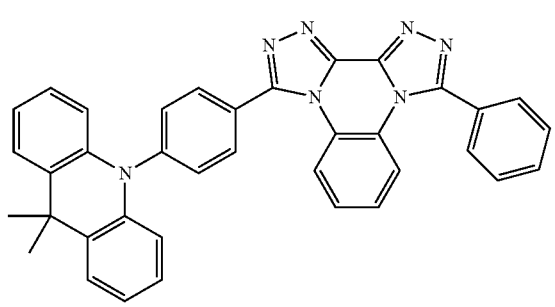
24
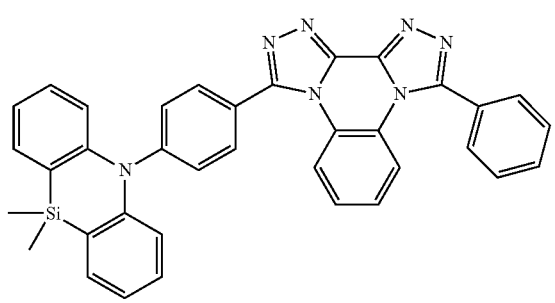
25
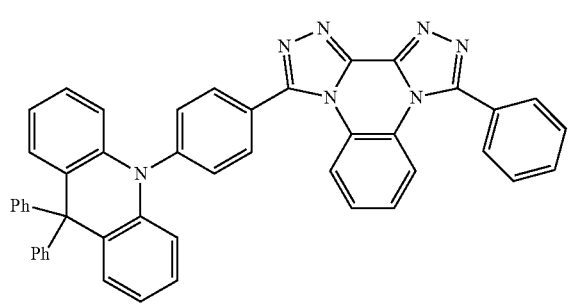
26
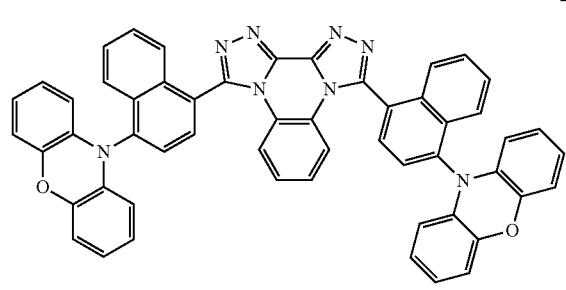
27
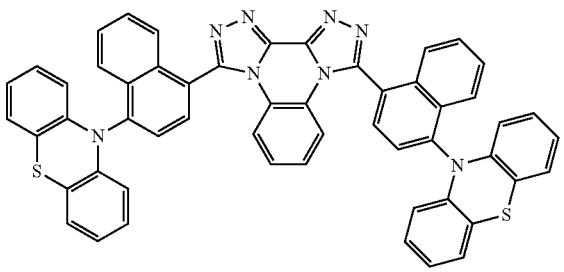
28
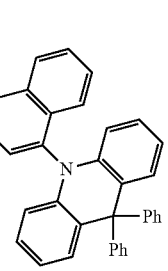
29
30
31

32
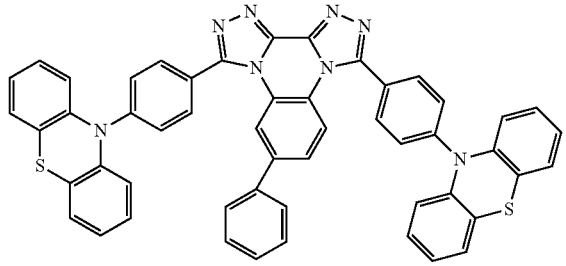

33
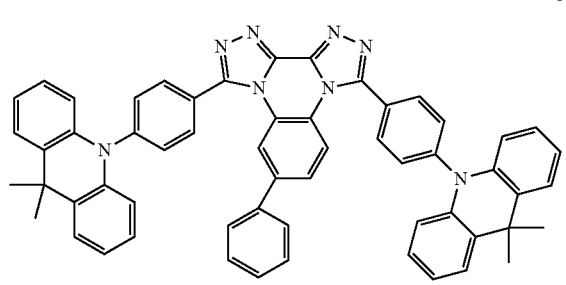

34
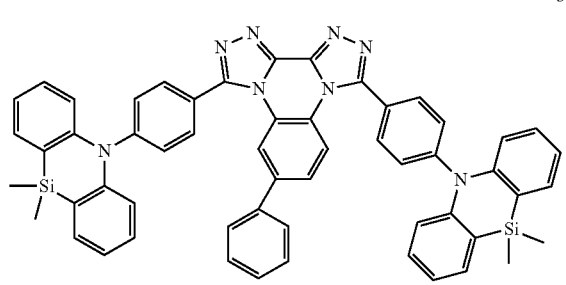

35
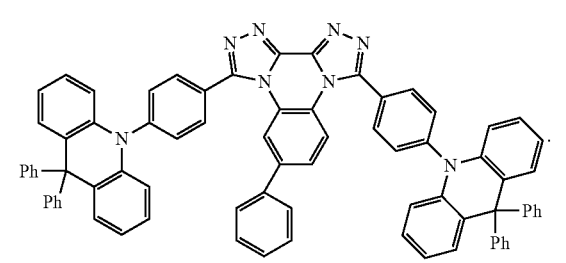

7. The compound according to claim 1, wherein:
an energy difference between a lowest singlet excited state $S_1$ and a lowest triplet excited state $T_1$ of the compound is configured to be $\Delta Est$, wherein $\Delta Est \leq 0.30$ eV.

8. The compound according to claim 7, wherein:
the energy difference between the lowest singlet excited state $S_1$ and the lowest triplet excited state $T_1$ of the compound is configured to be $\Delta Est$, wherein $\Delta Est \leq 0.02$ eV.

9. The compound according to claim 1 is configured to emit light by absorbing energy generated by an electron-hole recombination.

10. An organic optoelectronic device, comprising:
an anode;
a cathode; and
one or more organic thin film layers disposed between the anode and the cathode,
wherein at least one of the one or more organic thin film layers includes one or more compounds each having the following chemical formula (I):

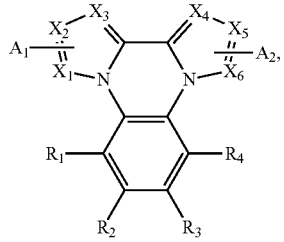

formula (I)

wherein: in the chemical formula (I),
$R_1$ to $R_{10}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl,
$X_1$ to $X_6$ are independently selected from C and N, when N is selected, N does not include a substituent, and when C is selected, C includes a substituent selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$, at least one of $X_1$ to $X_3$ and at least one of $X_4$ to $X_6$ are selected as C and, meanwhile, connected to $A_1$ and $A_2$, respectively, and
$A_1$ and $A_2$ are chemical groups independently represented by the following chemical formula (II):

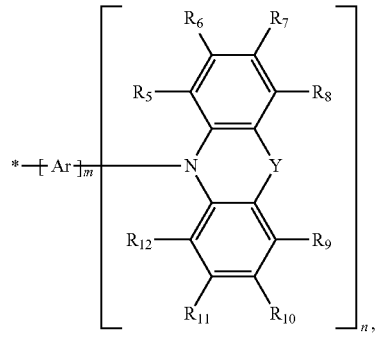

formula (II)

wherein: in the chemical formula (II),
$R_5$ to $R_{12}$ are independently selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl,
Y is selected from O, S, substituted or unsubstituted imino, substituted or unsubstituted methylene, substituted or unsubstituted silylene, and a substituent is selected from hydrogen, deuterium, $C_1$ to $C_{30}$ alkyl, $C_1$ to $C_{30}$ heteroatom-substituted alkyl, $C_6$ to $C_{30}$ aryl, and $C_2$ to $C_{30}$ heteroaryl,
Ar is selected from $C_6$ to $C_{30}$ aryl and $C_2$ to $C_{30}$ heteroaryl,
m represents 0 or 1, and n represents 0 or 1, and
n in $A_1$ and n in $A_2$ are not zero at the same time.

11. The organic optoelectronic device according to claim 10, wherein:
the one or more compounds are heat activated delayed fluorescence (TADF) materials.

12. The organic optoelectronic device according to claim 10, wherein:
the at least one of the one or more organic thin film layers disposed between the anode and the cathode is a light-emitting layer, wherein the light-emitting layer includes the one or more compounds.

13. The organic optoelectronic device according to claim 12, wherein:
the one or more compounds are used as a dopant material, a co-doping material, or a host material in the light-emitting layer.

14. The organic optoelectronic device according to claim 10, wherein:
the one or more organic thin film layers further include at least one of a hole transport layer, a hole injection layer, an electron blocking layer, a hole blocking layer, an electron transport layer, and an electron injection layer.

15. The organic optoelectronic device according to claim 14, wherein:
at least one of the hole transport layer, the hole injection layer, the electron blocking layer, the hole blocking layer, the electron transport layer, and the electron injection layer includes the one or more compounds.

16. The organic optoelectronic device according to claim 14, wherein:
the one or more organic thin film layers further include the hole transport layer disposed between the light-emitting layer and the anode.

17. The organic optoelectronic device according to claim 14, wherein:
the one or more organic thin film layers further include the hole transport layer and the electron transport layer, wherein the hole transport layer is disposed between the light-emitting layer and the anode, and
the electron transport layer is disposed between the light-emitting layer and the cathode.

18. The organic optoelectronic device according to claim 14, wherein:
the one or more organic thin film layers further include the hole transport layer, the electron transport layer, the electron injection layer and the hole injection layer,
wherein the hole transport layer and the hole injection layer are disposed between the light-emitting layer and the anode, and
the electron transport layer and the electron injection layer are disposed between the light-emitting layer and the cathode.

19. The organic optoelectronic device according to claim 14, wherein:
the one or more organic thin film layers further include the hole transport layer, the electron transport layer, the electron injection layer, the hole injection layer, the electron blocking layer, and the hole blocking layer,
wherein the electron blocking layer, the hole transport layer and the hole injection layer are disposed between the light-emitting layer and the anode, and
the hole blocking layer, the electron transport layer and the electron injection layer are disposed between the light-emitting layer and the cathode.

* * * * *